United States Patent
Shi et al.

(10) Patent No.: US 9,315,809 B2
(45) Date of Patent: Apr. 19, 2016

(54) DIFFERENTIALLY EXPRESSED MICRORNA MOLECULES FOR THE TREATMENT AND DIAGNOSIS OF CANCER

(71) Applicant: CITY OF HOPE, Duarte, CA (US)

(72) Inventors: Yanhong Shi, Duarte, CA (US); Ming-Fei Lang, Duarte, CA (US); Chunnian Zhao, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/014,217

(22) Filed: Aug. 29, 2013

(65) Prior Publication Data

US 2014/0088170 A1  Mar. 27, 2014

Related U.S. Application Data

(60) Provisional application No. 61/694,698, filed on Aug. 29, 2012.

(51) Int. Cl.
| | |
|---|---|
| C07H 21/02 | (2006.01) |
| C12N 15/11 | (2006.01) |
| A61K 48/00 | (2006.01) |
| C12N 15/113 | (2010.01) |
| C12Q 1/68 | (2006.01) |
| G01N 33/574 | (2006.01) |

(52) U.S. Cl.
CPC ............ *C12N 15/113* (2013.01); *C12Q 1/6886* (2013.01); *G01N 33/574* (2013.01); *C12N 2310/113* (2013.01); *C12N 2310/141* (2013.01); *C12N 2330/10* (2013.01); *C12N 2330/50* (2013.01); *C12Q 2600/106* (2013.01); *C12Q 2600/178* (2013.01)

(58) Field of Classification Search
None
See application file for complete search history.

(56) References Cited

PUBLICATIONS

Nohata et al. (British Journal of Cancer (2011) 105, 833-841).*
Narita et al. (Oncogene (2005) 24, 7346-7354).*
Yoon et al. (J Cell Biochem. Nov. 1, 2009; 108(4): 832-838).*
Suh et al. (Proc. Nat. Acad. Sci. USA 109(14): 5316-5321, Apr. 3, 2012).*
Ambros, V. (2004) The functions of animal microRNAs. *Nature* 431:350-355.
Asadi-Moghaddam, K., Chiocca, E.A., Lawler, S.E. (2010) Potential role of miRNAs and their inhibitors in glioma treatment. *Expert Review of Anticancer Therapy* 10:1753-1762.
Bao, S., Wu, Q., et al. (2006) Glioma stem cells promote radioresistance by preferential activation of the DNA damage response. *Nature* 444:756-760.
Bartel, D.P. (2004) MicroRNAs: genomics, biogenesis, mechanism, and function. *Cell* 116:281-297.
Bloomston, M., Frankel, W.L., et al. (2007) MicroRNA expression patterns to differentiate pancreatic adenocarcinoma from normal pancreas and chronic pancreatitis. *JAMA* 297:1901-1908.
Brault, L., Gasser, C., et al. (2010) PIM serine/threonine kinases in the pathogenesis and therapy of hematologic malignancies and solid cancers. *Haematologica* 95:1004-1015.
Brown, C.E., Starr, R., et al. (2009) Recognition and killing of brain tumor stem-like initiating cells by CD8+ cytolytic T cells. *Cancer Research* 69:8886-8893.
Calin, G.A., Liu C.G., et al. (2004) MicroRNA profiling reveals distinct signatures in B cell chronic lymphocytic leukemias. *Proceedings of the National Academy of Sciences.* 101:11755-11760.
Cheng, L., Bao, S., Rich, J.N. (2010) Potential therapeutic implications of cancer stem cells in glioblastoma. *Biochemical Pharmacology* 80:654-665.
Ciafre, S.A., Galardi, S., et al. (2005) Extensive modulation of a set of microRNAs in primary glioblastoma. *Biochemical and Biophysical Research Communications* 334:1351-1358.
Clayton, P.E., Banerjee, I., Murray, P.G., Renehan, A.G. (2011) Growth hormone, the insulin-like growth factor axis, insulin and cancer risk. *Nat Rev Endocrinol* 7:11-24.
Conti, A., Aguennouz, M., et al. (2009) miR-21 and 221 upregulation and miR-181b downregulation in human grade II-IV astrocytic tumors. *Journal of Neuro-oncology* 93:325-332.
Ebert, M.S., Neilson, J.R., Sharp, P.A., (2007) MicroRNA sponges: competitive inhibitors of small RNAs in mammalian cells. *Nat Methods* 4(9):721-6.
Esquela-Kerscher, A., Slack, F.J. (2006) Oncomirs—microRNAs with a role in cancer. *Nat Rev Cancer* 6:259-269.
Fowler, A., Thomson, D., et al. (2011) miR-124a is frequently downregulated in glioblastoma and is involved in migration and invasion. *Eur J Cancer* 47:953-963.
Furuta, M., Kozaki, K.I., et al. (2010) miR-124 and miR-203 are epigenetically silenced tumor-suppressive microRNAs in hepatocellular carcinoma. *Carcinogenesis* 31:766-776.
Gabriely, G., Yi, M., et al. (2011) Human glioma growth is controlled by microRNA-10b. *Cancer Research* 71:3563-3572.
Gal, H., Pandi, G., et al. (2008) MIR-451 and Imatinib mesylate inhibit tumor growth of Glioblastoma stem cells. *Biochemical and Biophysical Research Communications* 376:86-90.
Godlewski, J., Newton, H.B., Chiocca, E.A., Lawler, S.E. (2010) MicroRNAs and glioblastoma; the stem cell connection. *Cell Death and Differentiation* 17:221-228.

(Continued)

*Primary Examiner* — Richard Schnizer
(74) *Attorney, Agent, or Firm* — Perkins Coie LLP

(57) ABSTRACT

A significant challenge in cancer research field is to define molecular features that distinguish cancer stem cells from normal stem cells. In this study, microRNA (miRNA) expression profiles in human glioblastoma stem cells were compared to that of normal neural stem cells using combined microarray and deep sequencing analyzes. These studies led to the identification of several miRNAs that are differentially expressed in glioblastoma stem cells and normal neural stem cells. Characterizing the role of these miRNAs in glioblastoma stem cells is important for the development of miRNA-based therapies that specifically target tumor stem cells, but spare normal stem cells.

4 Claims, 7 Drawing Sheets

(56) References Cited

PUBLICATIONS

Godlewski, J., Nowicki, M.O., et al. (2008) Targeting of the Bmi-1 oncogene/stem cell renewal factor by microRNA-128 inhibits glioma proliferation and self-renewal. *Cancer Research* 68:9125-9130.

Hunt, S., Jones, A.V., Hinsley, E.E., Whawell, S.A., Lambert, D.W. (2011)/MicroRNA-124 suppresses oral squamous cell carcinoma motility by targeting ITGB1. *FEBS Letters* 585:187-192.

Huse, J.T., Brennan, C., et al. (2009) The PTEN-regulating microRNA miR-26a is amplified in high-grade glioma and facilitates gliomagenesis in vivo. *Genes & Development* 23:1327-1337.

Junttila, M.R., Evan, G.I. (2009) p53—a Jack of all trades but master of none. *Nat Rev Cancer* 9:821-829.

Kamal, M., Shaaban, A.M., et al. (2010) Loss of CSMD1 expression is associated with high tumour grade and poor survival in invasive ductal breast carcinoma. *Breast Cancer Research and Treatment* 121:555-563.

Kan, Z., Jaiswal, B.S., et al. (2010) Diverse somatic mutation patterns and pathway alterations in human cancers. *Nature* 466:869-873.

Kiessling, M.K., Oberholzer, P.A., et al. (2011) High-throughput mutation profiling of CTCL samples reveals KRAS and NRAS mutations sensitizing tumors toward inhibition of the RAS/RAF/MEK signaling cascade. *Blood* 117:2433-2440.

Kim, H., Huang, W., et al. (2010) Integrative genome analysis reveals an oncomir/oncogene cluster regulating glioblastoma survivorship. *Proceedings of the National Academy of Sciences* 107:2183-2188.

Lewis, B.P., Shih, I.H., Jones-Rhoades, M.W., Bartel, D.P., Burge, C.B. (2003) Prediction of mammalian microRNA targets. *Cell* 115:787-798.

Li, K.K., Pang, J.C., et al. (2009) miR-124 is frequently down-regulated in medulloblastoma and is a negative regulator of SLC16A1. *Human Pathology* 40:1234-1243.

Louis, D.N., Ohgaki, H., et al. (2007) The 2007 WHO classification of tumours of the central nervous system. *Acta Neuropathologica* 114:97-109.

Ma, L., Teruya-Feldstein, J., Weinberg, R.A. (2007) Tumour invasion and metastasis initiated by microRNA-10b in breast cancer. *Nature* 449:682-688.

Ming, G.L., Song, H. (2011) Adult neurogenesis in the mammalian brain: significant answers and significant questions. *Neuron* 70:687-702.

Rao, S.A., Santosh, V., Somasundaram, K. (2010) Genome-wide expression profiling identifies deregulated miRNAs in malignant astrocytoma. *Mod Pathol* 23:1404-1417.

Roth, P., Wischhusen, J., et al. (2011) A specific miRNA signature in the peripheral blood of glioblastoma patients. *Journal of Neurochemistry* 118:449-457.

Shi, Y., Zhao, X., et al. (2010) MicroRNA regulation of neural stem cells and neurogenesis. *Journal of Neuroscience* 30: 14931-14936.

Silber, J., Lim, D.A., et al. (2008) miR-124 and miR-137 inhibit proliferation of glioblastoma multiforme cells and induce differentiation of brain tumor stem cells. *BMC Medicine* 6:14.

Singh, S.K., Hawkins, C., et al. (2004) Identification of human brain tumour initiating cells. *Nature* 432:396-401.

Skalsky, R.L., Cullen, B.R. (2011) Reduced expression of brain-enriched microRNAs in glioblastomas permits targeted regulation of a cell death gene. *PloS One* 6:e24248.

Sun, G., Ye, P., et al. (2011) miR-137 forms a regulatory loop with nuclear receptor TLX and LSD1 in neural stem cells. *Nature Communications* 2:529. DOI:10.1038/ncomms1532.

Sun, G., Yu, R., Evans, R.M., Shi, Y. (2007) Orphan nuclear receptor TLX recruits histone deacetylases to repress transcription and regulate neural stem cell proliferation. *Proceedings of the National Academy of Sciences* 104:15282-15287.

Verissimo, C.S., Molenaar, J.J., Fitzsimons, C.P., Vreugdenhil, E. (2011) Neuroblastoma therapy: what is in the pipeline? *Endocrine-related Cancer* 18:R213-231.

Wu, Y., Wang, Y.Y., et al. (2010) Accelerated hepatocellular carcinoma development in mice expressing the Pim-3 transgene selectively in the liver. *Oncogene* 29:2228-2237.

Xia, H., Cheung, W.K., et al. (2012) Loss of brain-enriched miR-124 enhances the stem-like traits and invasiveness of glioma cells. *The Journal of Biological Chemistry* 287:9962-9971.

Zhao, C., Sun, G., Li, S., Lang, M-F, Yang, S., Li, W., Shi, Y. (2010) MicroRNA let-7b regulates neural stem cell proliferation and differentiation by targeting nuclear receptor TLX signaling. *Proceedings of the National Academy of Sciences* 107:1876-1881.

Zhao, C., Sun, G., Li, S., Shi, Y. (2009) A feedback regulatory loop involving microRNA-9 and nuclear receptor TLX in neural stem cell fate determination. *Nature Structural & Molecular Biology* 16:365-371.

Zhou, J., Neff, C.P., et al. (2011) Systemic administration of combinatorial dsiRNAs via nanoparticles efficiently suppresses HIV-1 infection in humanized mice. *Mol Ther* 19:2228-2238.

Zhou, J., Wu, J., et al. (2006) PAMAM dendrimers for efficient siRNA delivery and potent gene silencing. *Chem Commun* 22:2362-2364.

\* cited by examiner

A

```
     3' CCGUAAGUGGCG---CACGGAAU 5'  hsa-miR-124    SEQ ID NO:35
          | ||||| |:  |||||||
625:5'  AACUUCACAGUGAAGUGCCUUU  3'  human NRAS    SEQ ID NO:8
585:5'  AACAUUCACAACAAAGUGCCUUU 3'  mouse NRAS    SEQ ID NO:9
637:5'  AACUCUUGCAGCAAAGUGCCUUU 3'  dog   NRAS    SEQ ID NO:10
```

E

```
     3' CCGUAAGUG--GCGCACGGAAU 5'  hsa-miR-124    SEQ ID NO:35
         | |||:|  :| |||||||
127:5'  GACCUUCGCUUUGAGUGCCUUU 3'  human PIM3     SEQ ID NO:11
104:5'  GACCUUUGCUUUGAGUGCCUUU 3'  mouse PIM3     SEQ ID NO:12
```

DIFFERENTIALLY EXPRESSED MICRORNA MOLECULES FOR THE TREATMENT AND DIAGNOSIS OF CANCER

CROSS REFERENCE TO RELATED APPLICATIONS

This application claims the benefit of U.S. Provisional Patent Application No. 61/694,698, filed Aug. 29, 2012, which is incorporated herein by reference in its entirety.

STATEMENT OF GOVERNMENT INTEREST

The present invention was made with government support under R01-NS059546 and RC1-NS068370, each awarded by the National Institutes of Health and the National Institute of Neurological Disorders and Stroke (NIH NINDS). The Government has certain rights in the invention.

BACKGROUND

MicroRNAs (miRNAs) are short 20-22 nucleotide RNA molecules that are expressed in a tissue-specific and developmentally-regulated manner and function as negative regulators of gene expression in a variety of eukaryotes. miRNAs are involved in numerous cellular processes including development, proliferation, and differentiation [Ambros 2004; Bartel 2004; Shi et al. 2010]. Increasing evidence has linked miRNAs to cancer [Esquela-Kerscher & Slack 2006] and are important regulators of many key pathways implicated in tumor pathogenesis [Asadi-Moghaddam et al. 2010], functioning as oncogenes or tumor suppressors in various tumors [Cheng et al. 2010].

Although miRNAs have been shown to be differentially expressed in various types of cancer cells as compared to normal cells, many cancers are thought to be maintained by a population of cancer stem cells that retain stem cell properties, are highly tumorigenic, and display increased resistance to radiation and chemotherapy. As such, cancer therapies should target tumor stem cells, but spare normal stem cells. Therefore, there is a need for identifying miRNA molecules that are differentially expressed in tumor stem cell subpopulations as compared to normal stem cells for the development of miRNA-based cancer therapeutics and diagnostics.

SUMMARY

One embodiment, methods for treating a cancer are provided. In certain embodiments, such methods include administering a therapeutically effective amount of a pharmaceutical composition to a subject having the cancer, wherein the pharmaceutical composition comprises one or more therapeutic agents which target one or more miRNA molecules that are differentially expressed in cancer stem cells as compared to normal cells. In other embodiments, such methods include contacting a cancer cell or cancer stem cell with one or more miRNA molecules that have or impart at least one tumor suppressor activity.

In another embodiment, methods for diagnosing a cancer are provided. Such methods include detecting a test level of one or more miRNA molecules in a biological sample from a subject; comparing the test level to a reference level; and diagnosing the subject as having the cancer when the test level is significantly different than the reference level.

In another embodiment, an miRNA expression signature is provided that is specific to a cancer stem cell. The miRNA expression signature includes one or more miRNA molecules that are differentially expressed in the cancer stem cell.

According to the embodiments described above, the one or more miRNA molecules may be selected from miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, miR-450b-5p, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p.

The embodiments described above may be specific to and may be used to treat or diagnose any applicable cancer including, but not limited to, bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In one embodiment, the cancer is brain cancer, in particular, glioblastoma.

BRIEF DESCRIPTION OF THE DRAWINGS

FIG. 1A shows representative images of neurospheres from normal human neural stem cell lines 1-3 (NSC1-3) and glioblastoma stem cell lines 1-3 (GSC1-3). FIG. 1B illustrates the multipotency of NSCs and GSCs. When induced into differentiation, both NSCs and GSCs gave rise to Tuj1+ neurons (green) and GFAP+ astrocytes (red). Representative images of NSC1 and GSC1 differentiation were shown. Nuclear Dapi staining was shown in blue. FIG. 1C. H&E staining of coronal sections from GSC-transplanted brains. The tumor region was indicated by an arrow, shown in dark purple color.

FIGS. 4A and 4B show the base-pairing of hsa-miR-10a (SEQ ID NO: 1) and hsa-miR-10b (SEQ ID NO: 6) with the 3' UTR of CSMD1 gene (SEQ ID NOS: 2-5). FIG. 4C illustrates miR-10a-mediated repression of luciferase reporter gene downstream of 3' UTR of CSMD1. Luciferase reporter gene under the control of wild type (WT) or mutant (MT) CSMD1 3' UTR was transfected into HEK 293 cells along with control, miR-10a RNA duplexes, or the combination of miR-10a RNA duplexes and a miR-10a inhibitor. * p<0.001 by student's t-test. FIG. 4D illustrates miR-10b-mediated repression of luciferase reporter gene downstream of 3' UTR of CSMD1. WT or MT CSMD1 3' UTR luciferase reporter was transfected into HEK 293 cells along with control, miR-10b RNA duplexes, or the combination of miR-10b RNA duplexes and a miR-10b inhibitor. * p<0.005 by student's t-test. FIG. 4E illustrates expression of CSMD1 in glioblastoma stem cell line 1 (GSC) and neural stem cell line 1 (NSC) determined by real-time RT-PCR analysis. FIG. 4F illustrates expression of HOXD10 in GSC and NSC determined by real-time RT-PCR analysis. For all panels, data shown are mean±standard deviation of three replicates. ** p<0.01 by student's t-test for both panels E and F. The term "hsa" in front of the miRNA indicates the species *homo sapiens*.

FIG. 5A illustrates the base-pairing of hsa-miR-124 (SEQ ID NO: 7) with the 3' UTR of NRAS gene (SEQ ID NO: 8-10). FIG. 5B illustrates the miR-124-mediated repression of luciferase reporter gene downstream of 3' UTR of NRAS. Luciferase reporter gene under the control of wild type (WT) or mutant (MT) NRAS 3' UTR was transfected into HEK 293 cells along with control, miR-124 RNA duplexes, or the combination of miR-124 RNA duplexes and a miR-124 inhibitor. *p<0.001 by student's t-test. FIG. 5C illustrates Western blot analysis of NRAS expression in control RNA, miR-124 RNA duplexes, or the combination of miR-124 RNA duplexes and a miR-124 inhibitor-transfected GSC1 cells. FIG. 5D illustrates expression of NRAS in GSC1 and NSC1 determined by real-time RT-PCR analysis. *p<0.05 by student's t-test. FIG. 5E shows the base-pairing of hsa-miR-124 (SEQ ID NO: 7) with the 3' UTR of PIM3 gene (SEQ ID NO: 11-12). FIG. 5F illustrates miR-124-mediated repression of luciferase reporter gene downstream of 3' UTR of PIM3. Luciferase reporter gene under the control of wild type (WT) or mutant (MT) PIM3 3' UTR was transfected into HEK 293 cells along with control, miR-124 RNA duplexes, or the combination of miR-124 RNA duplexes and a miR-124 inhibitor. *p<0.001 by student's t-test. FIG. 5G illustrates Western blot analysis of PIM3 expression in control RNA, miR-124 RNA duplexes, or the combination of miR-124 RNA duplexes and a miR-124 inhibitor-transfected GSC1 cells. FIG. 5H illustrates the expression of PIM3 in GSC1 and NSC1 determined by real-time RT-PCR analysis. **p<0.001 by student's t-test. For all panels, data shown are mean±standard deviation of three replicates.

FIG. 6A illustrates that the up-regulated miRNAs in glioblastoma stem cells were predicted to target the p53 pathway. The p53-centered pathway has been shown to regulate cell cycle, apoptosis, angiogenesis, metastasis, and genome stability. FIG. 6B illustrates that the down-regulated miRNAs were predicted to target components of the IGF pathway. Various components of the IGF signaling pathways were targeted by down-regulated miRNAs. The IGF pathway has been shown to enhance cell growth, survival, and migration.

DETAILED DESCRIPTION

Figure 1:
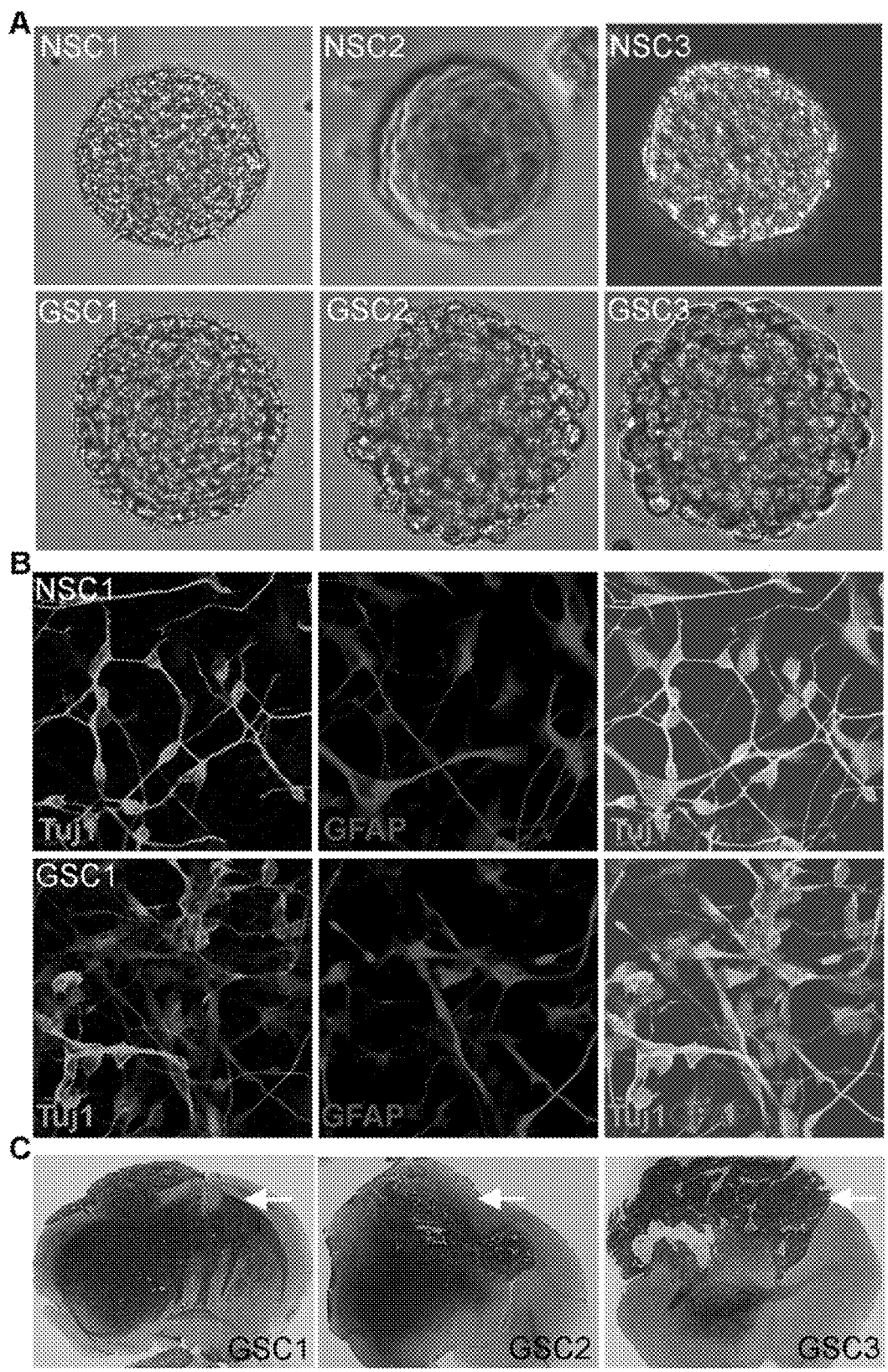
FIGS. 1A-1C show the morphology, differentiation and a growth curve of glioblastoma stem cells (GSCs) and neural stem cells (NSCs).

Methods for diagnosing and treating cancer using one or more miRNA molecules are provided herein. Such methods may be used to treat or diagnose any cancer or tumor cell type including bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., primary or metastatic cancers) or benign (e.g., hyperplasia, cyst, pseudocyst, hematoma, and benign neoplasm).

In one embodiment, the methods described herein may be used to treat or diagnose a brain cancer including, but not limited to, gliomas (e.g., astrocytomas, oligodiendrogliomas, mixed gliomas, enendymomas, brain stem gliomas) meningiomas, pineal gland and pituitary gland tumors, primary central nervous system lymphomas, medulloblastomas, craniopharyngiomas and acoustic neuromas.

Astrocytomas, the most common type of glioma, have been subclassified into four subtypes ("or grades") using the World Health Organization (WHO) classification system for tumor identification [Louis et al. 2007]. This grading scheme represents a malignancy scale and is an important factor influencing the choice of therapies. According to the WHO, a grade I astrocytoma is classified as a pilocytic astrocytoma, a grade II astrocytoma is classified as a diffuse astrocytoma, a grade III astrocytoma is classified as an anaplastic astrocytoma, and a grade IV astrocytoma is classified as a glioblastoma—the most malignant grade [Louis et al. 2007]. Glioblastoma is the most common and aggressive primary brain tumor with median survival time of 14 months after diagnosis [Louis et al. 2007]. Currently, no effective treatment has been developed for glioblastoma patients. Therefore, although the miRNA molecules used according to the methods described herein may be used to treat or diagnose any type of cancer, the Examples are primarily directed to the identification of miRNA molecules related to glioblastoma.

Recent studies have suggested that glioblastomas are maintained by a small population of cancer stem cells that retain stem cell properties, are highly tumorigenic, and display increased resistance to radiation and chemotherapy [Singh et al. 2004; Bao et al. 2006; Godlewski et al. 2010]. These treatment-resistant tumor cell subpopulations are the cell populations that effective therapies must target [Godlewski et al. 2010].

miRNAs have been shown to be differentially expressed in glioblastoma tissues compared to normal brain tissues. For example, miRNA 21 is overexpressed in glioblastoma tissues, relative to surrounding normal brain tissues [Conti et al. 2009]. miR-26a is also amplified in glioblastoma tissues. By targeting the tumor suppressor Pten, overexpression of miR-26a facilitates tumorigenesis and predicts a poor survival [Huse et al. 2009; Kim et al. 2010]. On the other hand, miR-124, miR-137 and miR-451 exhibit reduced expression in malignant glioblastoma tissues relative to normal brain tissues [Silber et al. 2008; Gal et al. 2008]. The expression of these miRNAs is also reduced in glioblastoma stem cells relative to bulk tumor cells. Overexpression of these miRNAs in glioblastoma stem cells inhibits cell proliferation and induces neural differentiation, suggesting a tumor suppressor role for these miRNAs. These studies suggest that some miRNAs may be used as therapeutic agents for targeting glioblastoma stem cells. However, brain tumor stem cells share a core developmental program with normal neural stem cells [Cheng et al. 2010]. Optimal therapies should be designed to target tumor stem cells, but spare normal stem cells. Therefore, identifying miRNAs that are differentially expressed in glioblastoma stem cells and normal neural stem cells is important for the development of optimal miRNA-based therapies and diagnostics for glioblastoma patients.

Therefore, in some embodiments, methods for treating cancer (e.g., glioblastoma) include a step of administering a therapeutically effective amount of a pharmaceutical composition that includes one or more therapeutic agents which target and/or affect the expression level of one or more miRNA molecules that are differentially expressed in cancer stem cells (e.g., glioblastoma stem cells) and/or other cancer cells as compared to healthy cells or healthy stem cells. A therapeutic agent which targets a target molecule (e.g., a target miRNA molecule that is differentially expressed) means that said therapeutic agent, when administered to a subject or is otherwise exposed to the target molecule, results in an alteration in the expression or activity of the target molecule. Such alteration may include, but is not limited to, inhibition, suppression activation, agonization, or otherwise cause a change in the expression or activity level of the target molecule. The therapeutic agent may directly cause such a change, or may act on upstream or downstream targets that ultimately result in a change to the target molecule.

According to some embodiments, the one or more miRNA molecules that are targeted may include, but are not limited to, miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, miR-450b-5p, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p.

In one embodiment, the one or more therapeutic agents target one or more miRNA molecules that are significantly upregulated in cancer stem cells (e.g., glioblastoma stem cells) and/or other cancer cells as compared to healthy cells or healthy stem cells. The one or more miRNA molecules that are significantly upregulated include, but are not limited to, miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, and miR-450b-5p. In one embodiment, the one or more miRNA molecules that are significantly upregulated include, but are not limited to miR-10a, miR-10b, miR-140-3p, miR-140-5p, miR-204, miR-424, miR-455-5p, miR-455-3p.

In another embodiment, the one or more therapeutic agents target one or more miRNA molecules that are significantly downregulated in cancer stem cells (e.g., glioblastoma stem cells) and/or other cancer cells as compared to healthy cells or healthy stem cells. The one or more miRNA molecules that are significantly downregulated include, but are not limited to, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p. In one embodiment, the one or more miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

In certain embodiments, treating cancer (e.g., glioblastoma) in a subject having the cancer may be accomplished by contacting a cancer cell (e.g., glioblastoma cell) or cancer stem cell (e.g., glioblastoma stem cell) with one or more miRNA molecules that have or impart at least one tumor suppressor activity. In such embodiments, the one or more miRNA molecules act as a therapeutic agent directly. Tumor suppressor activities may include, but are not limited to, suppression or inhibition of cell growth and/or cell division. In some examples, an miRNA that is found to be significantly down-regulated in cancer cells or cancer stem cells relative to normal stem cells or normal cells may act as a tumor suppressor. Thus, miRNA molecules that have or impart tumor suppressor activities may include, but are not limited to miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p. In one embodiment, the one or more miRNA molecules that have or impart tumor suppressor activities may include, but are not limited to, hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

In certain embodiments, the one or more therapeutic agents target at least one miRNA molecules that is significantly upregulated and at least one miRNA molecule that is significantly downregulated in cancer stem cells (e.g., glioblastoma stem cells) and/or other cancer cells as compared to healthy cells or healthy stem cells. The one or more miRNA molecules that are significantly upregulated include, but are not limited to miR-10a, miR-10b, miR-140-3p, miR-140-5p, miR-204, miR-424, miR-455-5p, miR-455-3p; and the one or more miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

Therapeutic agents that may be used in accordance with the methods described herein may include, but are not limited to, (i) miRNA inhibitors to inhibit or silence specific miRNA molecules that are upregulated in glioblastoma or other cancers; (ii) miRNA inhibitors to sequester endogenous miRNA, thereby blocking the endogenous miRNA function (i.e., the "sponge method," see Ebert et al. 2007, which is hereby incorporated by reference as if fully set forth herein); and (iii) agents that increase the level of specific miRNA molecules, for example, an miRNA that has been identified as a downregulated miRNA molecule to replace the same miRNA that has a lower expression (such as those described above) or an miRNA expression vector that causes a cell to overexpresses such a downregulated miRNA molecule; and (iv) miRNA molecules that can directly replace a downregulated miRNA molecule.

Because the sequences of many miRNA molecules have been previously described (see www.mirbase.org/), inhibitors specific for one or more upregulated miRNA molecules, such as those described above, may be obtained commercially (e.g., from Thermo Scientific Dharmacon), or may be developed based on designing microRNA hairpin inhibitors, antisense inhibitors (e.g., 2'-O-methyl miRNA antisense RNAs), LNA miRNA inhibitors, RNA interference molecules (e.g., shRNA, sRNA), aptamers, or other suitable complementary miRNA inhibitors.

Delivery of the therapeutic agents described above may be accomplished by any suitable method including, but not limited to, viral vector-delivery (e.g., lentiviral vector delivery, AAV-viral vector delivery, adenoviral vector delivery), dendrimer-mediated delivery, nanoparticle-mediated delivery or a combination thereof (e.g., dendrimer-based nanoparticle delivery).

In addition to the therapeutic agents, the pharmaceutical composition may also include a pharmaceutical carrier. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that outweighs its therapeutic benefits.

The pharmaceutical composition that may be used in accordance with the methods described herein may be administered, by any suitable route of administration, alone or as part of a pharmaceutical composition. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, an miRNA molecule or other biomarker that is either (i) upregulated or overexpressed; or (ii) downregulated or underexpressed can also be referred to as being "differentially expressed" as compared to a "normal" expression level or value of the miRNA molecule or other biomarker that indicates or is a sign of a normal process or an absence of a disease or other condition in an individual. Thus, "differential expression" of an miRNA molecule or other biomarker can also be referred to as a variation from a "normal" expression level of the biomarker. Differential expression includes quantitative, as well as qualitative, differences in the temporal or cellular expression pattern in a gene or its expression products among, for example, normal and diseased cells (e.g., normal stem cells vs. cancer stem cells; normal cells vs. cancer cells, or a combination thereof), or among cells which have undergone different disease events or disease stages.

Further, the phrase "differentially expressed" refers to a difference in the quantity or intensity of a marker (e.g., miRNA) present in a biological sample taken from subjects having a cancer as compared to a comparable sample taken from subjects who do not have the cancer. For example, an miRNA molecule is differentially expressed between the samples if the amount of the miRNA molecule in one sample is significantly different (i.e., $p<0.05$) from the amount of the miRNA molecule in the other sample. It should be noted that if the miRNA molecule or other marker is detectable in one sample and not detectable in the other, then the miRNA molecule can be considered to be differentially present.

The identification of the miRNAs described above and in the Examples below suggests that these miRNAs may be used as novel diagnostic markers. Thus, according to some embodiments, methods for diagnosing cancer (e.g., glioblastoma) include a step of detecting a test level of one or more miRNA molecules in a biological sample from a subject who is suspected of having the cancer.

According to some embodiments, the one or more miRNA molecules that are detected may include, but are not limited to, miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, miR-450b-5p, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p.

In one embodiment, the one or more miRNA molecules are significantly upregulated in cancer stem cells (e.g., glioblastoma stem cells) and/or other cancer cells as compared to healthy cells or healthy stem cells. The one or more miRNA molecules that are significantly upregulated include, but are not limited to, miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, and miR-450b-5p. In one embodiment, the one or more miRNA molecules that are significantly upregulated include, but are not limited to miR-10a, miR-10b, miR-140-3p, miR-140-5p, miR-204, miR-424, miR-455-5p, miR-455-3p.

In another embodiment, the one or more miRNA molecules are significantly downregulated in cancer stem cells (e.g., glioblastoma stem cells) and/or other cancer cells as compared to healthy cells or healthy stem cells. The one or more miRNA molecules that are significantly downregulated include, but are not limited to, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p. In one embodiment, the one or more miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

In certain embodiments, the one or more miRNA molecules may include at least one miRNA molecule that is significantly upregulated and at least one miRNA molecule that is significantly downregulated in cancer stem cells (e.g., glioblastoma stem cells) and/or other cancer cells as compared to healthy cells or healthy stem cells. The one or more miRNA molecules that are significantly upregulated include, but are not limited to miR-10a, miR-10b, miR-140-3p, miR-140-5p, miR-204, miR-424, miR-455-5p, miR-455-3p; and the one or more miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

According to the embodiments described herein, a biological sample may refer to any material, biological fluid, tissue, or cell obtained or otherwise derived from an individual including, but not limited to, blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, milk, bronchial aspirate, synovial fluid, joint aspirate, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. A biological sample may also include a biological tissue sample, such as a sample obtained by tissue biopsy or by surgical excision. A biological sample may also include materials derived from a tissue culture or a cell culture. Further, a biological sample may be derived by taking biological samples from a number of individuals and pooling them or pooling an aliquot of each individual's biological sample. The pooled sample can be treated as a sample from a single individual and if the presence of cancer is established in the pooled sample, then each individual biological sample can be re-tested to determine which individuals have cancer.

A test level of an miRNA molecule or other biomarker refers to an amount of a biomarker, such as an miRNA molecule, in a subject's undiagnosed biological sample. The test level may be compared to that of a control sample, or may be analyzed based on a reference or control level that has been previously established to determine a status of the sample. Such a status may be a diagnosis, prognosis or evaluation of a disease or condition. In one embodiment, the disease is cancer. A test sample or test amount can be either in absolute amount (e.g., nanogram/mL or microgram/mL) or a relative amount (e.g., relative intensity of signals).

The test level of the one or more miRNA molecules may be detected by any suitable method of measurement or quantification known in the art including, but not limited to, reverse transcriptase-polymerase chain reaction (RT-PCR) methods (including quantitative and qualitative RT-PCR methods), microarray, serial analysis of gene expression (SAGE), gene expression analysis by massively parallel signature sequencing (MPSS) or deep sequencing methods such as those described below, immunoassays such as ELISA, immunohistochemistry (IHC), mass spectrometry (MS) methods, transcriptomics and proteomics. Several of the detection methods described above include a transformative step, wherein the one or more miRNA molecules that are present in a biological sample are converted or transformed into structural, visual or other tangible manifestation of the amount of miRNA (e.g., a cDNA molecule, a reporter signal, a fluorescent, luminescent or radioactive signal, a labeled antibody, a graph, a tracing).

In some embodiments, the test level of the one or more miRNA molecules may be detected using a set of reagents which contain miRNA detection agents specific to a set of one or more miRNA molecules. The miRNA detection agents may be any suitable molecule that binds to and/or is complementary to the one or more miRNA molecules including, but not limited to, complementary oligonucleotides, antisense oligonucleotides, and aptamers. The set of reagents maybe used in accordance with any method of measurement or quantification, such as those described above, and/or may be provided in a kit for detecting the set of one or more miRNA molecules. According to some embodiments, the kit may include, in addition to the set of reagents which contain miRNA detection agents, at least one detection label to produce a detectable or visible signal (e.g., fluorescent labels, dyes, etc.), instructional materials, one or more reference standards, additional agents (e.g., buffers, stabilizers), vessels for storing or transporting the detection agents, or a combination thereof.

According to some embodiments, the test level is compared to a reference level (or a "reference standard") or a control level and the subject may then be diagnosed as having cancer when the test level is significantly different than the reference level or control level. A reference or control level of an miRNA molecule may be any amount or a range of amounts to be compared against the test level. For example, a reference or control level of an miRNA molecule may be the level detected in a population of patients with a specified condition or disease (e.g., malignancy, cancer or non-cancerous lung disease or condition) or the level detected in a control population of individuals without the condition or disease. A control amount can be either in absolute amount (e.g., nanogram/mL or microgram/mL) or a relative amount (e.g., relative intensity of signals).

In one embodiment, a test level of an miRNA molecule is considered to be significantly different than a reference or control level if said test level is at least 1.5-fold higher (i.e., upregulated) or lower (i.e., downregulated) as compared to a reference or control level of the miRNA. In some embodiments, the test level is considered to be significantly different than the reference or control level is the test level is at least 5-fold higher (i.e., upregulated) or lower (i.e., downregulated) as compared to the reference or control level. Alternatively, an increase or decrease in an mRNA molecule is typically significantly different if said increase or decrease has a p value of less than 0.5, or less than 0.05 (p<0.5 or p<0.05).

The one or more miRNA molecules described above may be part of an miRNA expression signature or profile that is specific to a cancer stem cell, such as those discussed above. Such an expression signature may be used in accordance with the methods herein to diagnose cancer, or may serve as a target for developing treatments for cancer. In one embodiment, the miRNA expression signature is specific to glioblastoma and includes, but is not limited to, one or more miRNA molecules selected from miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, miR-450b-5p, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p.

In another embodiment, the miRNA expression signature includes one or more miRNA molecules that are significantly upregulated in cancer stem cells (e.g., glioblastoma stem cells) and/or other cancer cells as compared to healthy cells or healthy stem cells. The one or more miRNA molecules that are significantly upregulated include, but are not limited to, miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a-4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, -miR-29a, miR-30d, miR-320, miR-181c, miR-128a, miR-21, let-7d, and miR-450b-5p. In one embodiment, the one or more miRNA molecules that are significantly upregulated include, but are not limited to miR-10a, miR-10b, miR-140-3p, miR-140-5p, miR-204, miR-424, miR-455-5p, miR-455-3p.

In another embodiment, the miRNA expression signature includes one or more miRNA molecules that are significantly downregulated in cancer stem cells (e.g., glioblastoma stem cells) and/or other cancer cells as compared to healthy cells or healthy stem cells. The one or more miRNA molecules that are significantly downregulated include, but are not limited to, miR-371-5p, miR-1245, miR-335, miR-492, miR-874, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p. In one embodiment, the one or more miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

In certain embodiments, the miRNA expression signature includes at least one miRNA molecule that is significantly upregulated and at least one miRNA molecule that is significantly downregulated in cancer stem cells (e.g., glioblastoma stem cells) and/or other cancer cells as compared to healthy cells or healthy stem cells. miRNA molecules that are significantly upregulated include, but are not limited to miR-10a, miR-10b, miR-140-3p, miR-140-5p, miR-204, miR-424, miR-455-5p, miR-455-3p; and miRNA molecules that are significantly downregulated include, but are not limited to hsa-miR-371-5p, hsa-miR-124-1, hsa-miR-124-2, hsa-miR-124-3, hsa-miR-335, hsa-miR-492, hsa-miR-874, hsa-miR-30b, and hsa-miR-602.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Identification of a Set of miRNAs that are Differentially Expressed in Glioblastoma Stem Cells and Normal Neural Stem Cells The Examples described below show the results of a genome-wide miRNA expression profiling study in human glioblastoma stem cells and normal neural stem cells using combined miRNA microarray and deep sequencing analyses. This study led to the identification of eight miRNAs that are substantially up-regulated and two miRNAs that are significantly down-regulated in glioblastoma stem cells, relative to normal neural stem cells. Differential expression of four of these miRNAs, 2 up-regulated and 2 down-regulated, was further validated by real-time RT-PCR in both glioblastoma stem cells and glioblastoma patient tumor tissues. Moreover, it was demonstrated that these up-regulated or down-regulated miRNAs inhibit the expression of genes that are involved in tumor suppression or tumorigenesis, respectively.

Materials and Methods

Ethics Statement.

The derivation of PBT003 (GSC1) and PBT017 (GSC2) has been described by Brown et al [Brown et al. 2009]. PBT707 (GSC3) is a de novo cell line derived from anonymized leftover tissues with the approval of the City of Hope Institutional Review Board. The study involves the use of completely anonymized specimens. No informed consent is involved. NOD-scid IL2Rgamma$^{null}$ (NSG) mice (6-8 weeks) were used for glioblastoma stem cell transplantation. Tumor cell transplantation was performed under an IACUC protocol approved by the City of Hope Institutional Animal Care and Use Committee.

Glioblastoma Stem Cell and Neural Stem Cell Culture.

Glioblastoma stem cells were derived from newly diagnosed WHO grade IV glioblastoma tissues. Specifically, freshly isolated glioblastoma tissues were minced with sterile scissors and dissociated into single cells using 400 units/ml of collagenase III in DMEM/F12 medium supplemented with 5 µg/ml heparin, 1×B27 (GIBCO/BRL), and 2 mM L-glutamine. Dissociated cells were then centrifuged at 1,200 rpm for 5 min and the supernatant was discarded. To eliminate red blood cells, the resultant cells were incubated in 10 ml red blood cell lysis buffer (Invitrogen) for 10 min. Cells were centrifuged again at 1,200 rpm for 5 min and supernatant was discarded. The resultant cells were resuspended in DMEM/F12 medium supplemented with 20 ng/ml EGF, 20 ng/ml FGF, 5 µg/ml heparin, 1×B27 (GIBCO/BRL), and 2 mM L-glutamine and cultured in this medium thereafter. Tumor spheres appeared around one week in culture. Normal human neural stem cells were derived from primary human brain tissues and maintained in the same culture media. Specifically, human fetal brain tissues (Biosciences Resources) were dissociated in cold Hanks balance salt solution (HBSS) using polished glass pipette. The resultant cells were centrifuged and resuspended in DMEM/F12 medium supplemented with 0.5×B27, 25 µg/ml insulin, 20 µg/ml apo-transferrin, 30 nM sodium selenite, 20 nM progesterone, 100 mM putrescine, 20 ng/ml FGF and 10 ng/ml LIF. The initial culture was split at 1:2 each day for 4 days, followed by media change every other day till day 21. Human neurospheres started to appear around day 14. The spheres were split around day 21 with Accutase (Sigma) and cultured in DMEM/F12 medium supplemented with 20 ng/ml EGF, 20 ng/ml FGF, 5 µg/ml heparin, 1×B27 (GIBCO/BRL), and 2 mM L-glutamine thereafter. Both tumor spheres and normal neurospheres were characterized for their self-renewal and multipotency. Glioblastoma stem cell spheres were also characterized for their ability to derive brain tumors.

For differentiation, both glioblastoma stem cells and neural stem cells were induced into differentiation using 0.5% fetal bovine serum and 1 µM all-trans retinoic acid. For in vivo tumor formation assays, $2 \times 10^5$ dissociated glioblastoma stem cells were injected into cerebral cortex of NSG mice by stereotaxic injection. The coordinates for the injection were AP 0.6 mm, ML +1.6 mm and DV −2.6 mm. Brains were harvested 5 weeks after cell transplantation. Frozen brains were cut into 20 µm coronal sections, followed by Hematoxylin & Eosin (H&E) staining.

Glioblastoma Stem Cell Transfection Using a Dendrimer-Based Delivery System.

Spheres of glioblastoma stem cells were dissociated and seeded into 24-well plates at $2 \times 10^5$ cells per well in 300 µl of medium. The generation-5 (G5) dendrimers and Opti-MEM solution were mixed by vortex for 10 seconds, and incubated at room temperature (RT) for 10 min. The miRNA duplexes or the combination of miRNAs and their short hairpin RNA inhibitors were added into dendrimer/Opti-MEM solution in a total volume of 100 µl, mixed gently for 10 sec, and incubated at RT for 25 min. The nitrogen-to-phosphorus (N/P) ratio of the dendrimer/RNA complex is 5. The 100 µl dendrimer/RNA complex was added into 300 µl cell suspension in each well of 24-well plates, shake gently and put back to $CO_2$ incubator. Forty-eight hr after transfection, cells were collected and subjected to Western blot analysis.

Western Blot Analysis.

Whole cell extracts of glioblastoma stem cells were prepared using RIPA buffer (50 mM Tris-HCl pH 7.5, 150 mM NaCl, 1% NP40, 0.5% deoxycholate and 0.1% SDS) containing protease inhibitor cocktail (Roche). Western blotting was performed with anti-NRAS (sc-31, 1:100) and anti-PIM3 (sc-98959, 1:100) antibodies from Santa Cruz.

Glioblastoma Stem Cell Transplantation.

NSG mice (6-8 weeks) were used for glioblastoma stem cell transplantation. Tumor cell transplantation was performed under the IACUC protocol 05050 approved by the City of Hope Institutional Animal Care and Use Committee. $5 \times 10^4$ dissociated glioblastoma stem cells were injected into the front lobe of forebrains by stereotaxic injection. The coordinates for the injection were AP 0.6 mm, ML +1.6 mm and DV −2.6 mm.

Reporter Construct Preparation.

DNA fragments encoding the 3' UTR of putative miRNA targets were cloned into psiCHECK 2 (Promega), downstream of a Renilla luciferase reporter gene. The PCR primers that were used for 3' UTR cloning of each gene are as follows: CSMD1 forward: 5' GAT CCT CGA GCT GTT CTG TCG CAG AAT G 3' (SEQ ID NO: 13) and CSMD1 reverse: 5' GAT CGC GGC CGC GTC AGC ATT TTG CAC CTA G3' (SEQ ID NO: 14); PIM3 forward: 5' GAT CCT CGA GGC TTG TGA GGA GCT GCA C 3' (SEQ ID NO: 15) and PIM3 reverse: 5' GAT CGC GGC CGC GGA AAC TTG TCA GGT CAC C 3' (SEQ ID NO: 16); NRAS forward: 5' GAT CCT CGA GCT GGA GGA GAA GTA TTC CTG 3' (SEQ ID NO: 17) and NRAS reverse: 5' GAT CGC GGC CGC TGC AAA TGT AGA GCT TTC TGG 3' (SEQ ID NO: 18). Corresponding miRNA binding sites on the 3' UTRs were mutated by site-directed mutagenesis according to the manufacturer's instructions (Stratagene). The binding site of hsa-miR-124 on the 3' UTR of PIM3 and NRAS was mutated from GTGCCTT to GTG<u>GACA</u>; the binding site of hsa-miR-10b on the 3' UTR of CSMD1 was mutated from ACAGGGT to ACAG<u>TCC</u>.

Transfection and Reporter Assay.

Plasmid DNA or DNA-miRNA mixture was transfected into HEK293 cells using Transfectin (Bio-Rad) as described [Zhao et al. 2009; Zhao et al. 2010; Sun et al. 2011]. miR-10a, miR-10b or miR-124 RNA duplexes and/or their correspondent RNA inhibitors (Dharmacon) were mixed in 50 µl serum free media with Transfectin, incubated at RT for 20 min. Negative controls for miRNA and their hairpin inhibitors were included. The final concentration of miRNAs or their inhibitors was 20 nM. The resultant mixture was added dropwise to HEK293 cells in a 24-well plate with 450 µl medium per well to a total volume of 500 µl per well. The transfected cells were harvested 48 h after transfection and subjected to subsequent reporter assays as described [Sun et al. 2007]. Reporter Renilla luciferase activity was measured 48 hrs after transfection using Dual Luciferase Assay kit (Promega). The Renilla luciferase activity was normalized by firefly luciferase internal control and expressed as relative luciferase activity. The miR-10a RNA duplex sense sequence is 5' TAC CCT GTA GAT CCG AAT TTG TG 3' (SEQ ID NO: 19). The miR-10b RNA duplex sense sequence is 5' TAC CCT GTA GAA CCG AAT TTG TG 3' (SEQ ID NO: 20). The miR-124 RNA duplex sense sequence is 5' TAA GGC ACG CGG TGA ATG CC 3' (SEQ ID NO: 21). And the control RNA duplex sense sequence is 5' UCA CAA CCU CCU AGA AAG AGU AGA 3' (SEQ ID NO: 22).

Real-Time RT-PCR Analysis.

For miRNA expression, total RNAs were reversely transcribed and quantified by real-time RT-PCR with TaqMan MicroRNA Assay kit (Applied Biosystems). The expression of specific miRNAs was normalized using human U18 snRNA. For mRNA expression, putative miRNA targets were quantified by iTaq SYBR Green Supermix with ROX (Bio-Rad). Primers used for RT-PCR include PIM3 forward: 5' AGC TCA AGC TCA TCG ACT TC 3' (SEQ ID NO: 23) and PIM3 reverse: 5' TAG CGG TGG TAG CGG ATC 3' (SEQ ID NO:24); NRAS forward: 5' CCA TGA GAG ACC AAT ACA TGA G 3' (SEQ ID NO: 25) and NRAS reverse: 5' GCT TAA TCT GCT CCC TGT AG 3' (SEQ ID NO: 26); HOXD10 forward: 5' TTC CCG AAG AGA GGA GCT G 3' (SEQ ID NO: 27) and HOXD10 reverse: 5' CTG CCA CTC TTT GCA GTG AG 3' (SEQ ID NO: 28); CSMD1 forward: 5' GCA GAA ATG CTT ACT GAG GAT G 3' (SEQ ID NO: 29) and CSMD1 reverse: 5' AGA ACC CTC AAA CTG CAA CTG 3' (SEQ ID NO: 30); GAPDH forward: 5' ATC ACC ATC TTC CAG GAG C 3' (SEQ ID NO: 31) and GAPDH reverse 5' CCT TCT CCA TGG TGG TGA AG 3' (SEQ ID NO: 32).

miRNA Microarray and Deep Sequencing Analysis.

Total RNAs were extracted from glioblastoma stem cells or human neural stem cells by TRIzol (Invitrogen) method according to manufacturer's protocol. Ten µg of RNA was used for miRNA microarray using Exiqon platform. One µg of RNA was used for deep sequencing using Illumina Genome Analyser II (GAII). All data are MIAME compliant.

Pathway Analysis.

Common putative targets of either the down-regulated or the up-regulated miRNAs were uploaded onto the Database for Annotation, Visualization and Integrated Discovery (DAVID) Functional Annotation Bioinformatics Microarray Analysis (david.abcc.ncifcrf.gov/). Kyoto Encyclopedia of Genes and Genomes (KEGG) pathway in DAVID was used to depict the biological meanings of the common miRNA targets.

Results

Differential miRNA Expression in Glioblastoma Stem Cells and Normal Neural Stem Cells.

To identify miRNAs that are differentially expressed in glioblastoma stem cells and normal neural stem cells, three primary glioblastoma stem cell lines and three normal human neural stem cell lines were established to determine if miRNA expression was significantly different in tumor stem cells as compared to normal stem cells. Human primary glioblastoma stem cells were derived from newly diagnosed glioblastoma multiforme IV patients and cultured in DMEM/F12 media supplemented with epithelial growth factor (EGF), fibroblast growth factor (FGF), and B27 supplement. Human normal neural stem cells were derived from normal human brain tissues and cultured in the same media. Both glioblastoma stem cells and normal neural stem cells grew as neurospheres under the culture conditions (FIG. 1A). Both types of cells are multipotent, having the ability to differentiate into Tuj1-positive neurons and/or GFAP-positive astrocytes when induced into differentiation using fetal bovine serum and all-trans retinoic acid (FIG. 1B). However, the glioblastoma stem cells were able to generate tumors when transplanted to the immunodeficient NSG mice (FIG. 1C), whereas the human neural stem cells did not (data not shown).

Combined microarray and deep sequencing analyses were performed to determine the expression profile of miRNAs in glioblastoma stem cells and normal neural stem cells. Total RNAs were prepared from both glioblastoma stem cells and neural stem cells for miRNA microarray analysis. In microarray analysis, 10 miRNAs were identified as having more than a 5-fold up-regulation in expression in glioblastoma stem cells and 8 miRNAs were identified as having more than a 5-fold down-regulation in expression in glioblastoma stem cells, relative to neural stem cells (Table 1). The differentially expressed miRNAs that exhibit more than 1.5-fold difference in the expression between glioblastoma stem cells and neural stem cells are shown in Table 2 below.

TABLE 1

Up-regulated and down-regulated miRNAs in human glioblastoma stem cells, compared to human neural stem cells.

| miRNA | Chromosomal location | Fold-Change | p-value |
|---|---|---|---|
| up-regulated | | | |
| hsa-miR-10a | 17q21.32 | 93.65 | 3.28E−10 |
| hsa-miR-10b | 2q31.1 | 90.38 | 2.06E−09 |
| hsa-miR-140-3p | 16q22.1 | 14.10 | 1.62E−10 |
| hsa-miR-140-5p | 16q22.1 | 12.19 | 5.56E−09 |
| hsa-miR-204 | 9q21.12 | 9.05 | 4.08E−08 |
| hsa-miR-424 | Xq26.3 | 8.38 | 2.53E−08 |
| hsa-miR-455-5p | 9q32 | 5.87 | 1.48E−05 |
| hsa-miR-455-3p | 9q32 | 5.41 | 9.32E−05 |
| down-regulated | | | |
| hsa-miR-371-5p | 19q13.42 | −15.27 | 8.52E−11 |
| hsa-miR-124-1* | 8p23.1 | | |
| hsa-miR-124-2* | 8q12.3 | −13.37 | 8.33E−05 |
| hsa-miR-124-3* | 20q13.33 | | |
| hsa-miR-335 | 7q32.2 | −13.24 | 1.43E−09 |
| hsa-miR-492 | 12q22 | −7.77 | 5.38E−08 |
| hsa-miR-874 | 5q31.2 | −6.76 | 1.53E−06 |
| hsa-miR-30b* | 8q24.22 | −6.54 | 2.73E−09 |
| hsa-miR-602 | 9q34.3 | −5.75 | 2.63E−08 |

*hsa-miR-124 is transcribed from three chromosomal locations, but the mature sequences are the same.

TABLE 2

Up-regulated and down-regulated miRNAs (>1.5 fold) in human glioblastoma stem cells, compared to human neural stem cells.

| miRNA | Chromosomal location | Fold-Change | p-value |
|---|---|---|---|
| Up-regulated | | | |
| hsa-miR-10a | 17q21.32 | 93.64622 | 3.28E−10 |
| hsa-miR-10b | 2q31.1 | 90.38293 | 2.06E−09 |
| hsa-miR-140-3p | 16q22.1 | 14.10262 | 1.62E−10 |
| hsa-miR-140-5p | 16q22.1 | 12.19325 | 5.56E−09 |
| hsa-miR-204 | 9q21.12 | 9.05353 | 4.08E−08 |
| hsa-miR-424 | Xq26.3 | 8.38382 | 2.53E−08 |
| hsa-miR-34a | 1p36.22 | 7.73283 | 2.21E−07 |
| hsa-miR-193a-3p | 17q11.2 | 6.39914 | 7.95E−06 |
| hsa-miR-455-5p | 9q32 | 5.87119 | 1.48E−05 |
| hsa-miR-455-3p | 9q32 | 5.40680 | 9.32E−05 |
| hsa-miR-9* | 1q22 | 4.43204 | 8.28E−08 |
| hsa-miR-10a* | 17q21.32 | 3.89600 | 1.92E−05 |
| hsa-miR-148a | 7p15.2 | 3.16202 | 1.93E−05 |
| hsa-miR-488 | 1q25.2 | 2.77759 | 1.69E−03 |
| hsa-miR-196a[1] | 17q21.32 | 2.76521 | 2.69E−03 |
| hsa-miR-182 | 7q32.2 | 2.75689 | 1.52E−03 |
| hsa-miR-96 | 7q32.2 | 2.61400 | 1.61E−03 |
| hsa-miR-193b | 16p13.12 | 2.57981 | 4.90E−06 |
| hsa-miR-27a | 19p13.13 | 2.53543 | 1.73E−07 |
| hsa-miR-196b | 7p15.2 | 2.50868 | 3.54E−03 |
| hsa-miR-10b* | 2q31.1 | 2.40614 | 8.55E−03 |
| hsa-miR-29b[2] | 7q32.3 | 2.39299 | 3.27E−07 |
| hsa-miR-23a | 19p13.13 | 2.34219 | 9.88E−08 |
| hsa-miR-107 | 10q23.31 | 2.31374 | 4.42E−07 |
| hsa-miR-542-3p | Xq26.3 | 2.28873 | 4.59E−03 |
| hsa-miR-9[3] | 1q22 | 2.24593 | 1.27E−07 |
| hsa-miR-365a[4] | 16p13.12 | 2.20050 | 2.54E−06 |
| hsa-miR-450a | Xq26.3 | 2.11076 | 1.43E−02 |
| hsa-miR-100 | 11q24.1 | 2.04624 | 5.71E−07 |
| hsa-miR-105 | Xq28 | 1.99529 | 3.86E−03 |
| hsa-miR-363 | Xq26.2 | 1.99346 | 1.23E−02 |
| hsa-miR-105* | 4q24 | 1.88156 | 1.57E−02 |
| hsa-miR-106b | 7q22.1 | 1.86896 | 5.63E−06 |
| hsa-miR-15b | 3q25.33 | 1.79677 | 3.00E−06 |
| hsa-miR-21 | 17q23.1 | 1.76837 | 3.03E−05 |
| hsa-miR-376c | 14q32.31 | 1.76028 | 5.72E−04 |
| hsa-miR-93 | 7q22.1 | 1.74398 | 6.15E−06 |
| hsa-miR-99b | 19q13.41 | 1.73839 | 1.77E−05 |
| hsa-miR-155 | 21q21.3 | 1.72212 | 1.59E−02 |
| hsa-miR-33a | 22q13.2 | 1.72056 | 8.82E−05 |
| hsa-miR-876-3p | 9p21.1 | 1.68669 | 4.45E−02 |
| hsa-miR-362-3p | Xp11.23 | 1.67653 | 4.12E−02 |
| hsa-miR-25 | 7q22.1 | 1.66555 | 1.31E−04 |
| hsa-let-7i | 12q14.1 | 1.66413 | 1.12E−05 |
| hsa-miR-423-3p | 17q11.2 | 1.64838 | 2.50E−04 |
| hsa-miR-34b | 11q23.1 | 1.62786 | 9.72E−05 |
| hsa-miR-16-2* | 3q25.33 | 1.62586 | 1.81E−03 |
| hsa-miR-29a | 7q32.3 | 1.61583 | 9.27E−06 |
| hsa-miR-30d | 8q24.2 | 1.61189 | 9.38E−04 |
| hsa-miR-320 | 8p21.3 | 1.60864 | 8.71E−05 |
| hsa-miR-181c | 19p13.13 | 1.56262 | 1.30E−02 |
| hsa-miR-128a | 2q21.3 | 1.55521 | 4.20E−02 |
| hsa-miR-21* | 17q23.1 | 1.54998 | 2.94E−02 |
| hsa-let-7d | 9q22.32 | 1.53430 | 1.10E−03 |
| hsa-miR-450b-5p | Xq26.3 | 1.53397 | 3.49E−02 |
| Down-regulated | | | |
| hsa-miR-371-5p | 19q13.42 | −15.26715 | 8.52E−11 |
| hsa-miR-124[5] | 8p23.1 | −13.37236 | 8.33E−05 |
| hsa-miR-335 | 7q32.2 | −13.23553 | 1.43E−09 |
| hsa-miR-492 | 12q22 | −7.76626 | 5.38E−08 |
| hsa-miR-874 | 5q31.2 | −6.76244 | 1.53E−06 |
| hsa-miR-30b* | 8q24.22 | −6.54116 | 2.73E−09 |
| hsa-miR-193a-5p | 17q11.2 | −5.76493 | 2.38E−08 |
| hsa-miR-602 | 9q34.3 | −5.74746 | 2.63E−08 |
| hsa-miR-346 | 10q23.2 | −5.69712 | 4.97E−02 |
| hsa-miR-663 | 20p11.1 | −5.37200 | 1.31E−02 |
| hsa-miR-25* | 7q22.1 | −4.97894 | 2.47E−06 |
| hsa-miR-219-5p[6] | 6p21.32 | −4.91797 | 5.92E−07 |
| hsa-miR-184 | 15q25.1 | −4.87568 | 4.42E−08 |
| hsa-miR-135a[7] | 3p21.1 | −4.87064 | 1.94E−07 |
| hsa-miR-584 | 5q32 | −4.60287 | 1.77E−08 |
| hsa-miR-665 | 14q32.2 | −4.35369 | 7.57E−09 |
| hsa-miR-638 | 19p13.2 | −3.47384 | 3.88E−04 |
| hsa-miR-503 | Xq26.3 | −3.43502 | 1.20E−08 |
| hsa-miR-628-3p | 15q21.3 | −3.42905 | 1.71E−07 |
| hsa-miR-381 | 14q32.31 | −3.33814 | 2.55E−07 |
| hsa-miR-7[8] | 9q21.32 | −2.91031 | 4.96E−04 |
| hsa-miR-92b | 1q22 | −2.90543 | 2.73E−07 |
| hsa-miR-149* | 2q37.3 | −2.87318 | 1.44E−03 |
| hsa-miR-135b | 1q32.1 | −2.87250 | 4.47E−07 |
| hsa-miR-302d* | 4q25 | −2.77368 | 2.82E−03 |
| hsa-miR-498 | 19q13.42 | −2.75015 | 2.70E−03 |
| hsa-miR-766 | Xq24 | −2.49979 | 1.89E−03 |
| hsa-miR-138[9] | 3p21.32 | −2.48259 | 9.79E−07 |
| hsa-miR-623 | 13q32.3 | −2.43864 | 3.92E−03 |
| hsa-miR-519c-5p | 19q13.42 | −2.38133 | 1.61E−05 |
| hsa-miR-182* | 7q32.2 | −2.26786 | 4.18E−02 |
| hsa-miR-494 | 14q32.31 | −2.15454 | 3.51E−06 |
| hsa-miR-129-5p[10] | 7q32.1 | −2.13428 | 6.47E−04 |
| hsa-miR-513-5p | 11q23.1 | −2.12005 | 9.55E−03 |
| hsa-miR-200b* | 1p36.33 | −2.04703 | 5.69E−05 |
| hsa-miR-634 | 17q24.2 | −2.02966 | 6.14E−06 |
| hsa-miR-654-5p | 14q32.31 | −2.01663 | 7.48E−04 |
| hsa-miR-518b | 19q13.42 | −1.98208 | 1.05E−03 |
| hsa-miR-658 | 22q13.1 | −1.94699 | 1.80E−06 |

TABLE 2-continued

Up-regulated and down-regulated miRNAs (>1.5 fold) in human glioblastoma stem cells, compared to human neural stem cells.

| miRNA | Chromosomal location | Fold-Change | p-value |
|---|---|---|---|
| hsa-miR-373* | 19q13.42 | −1.91189 | 4.25E−03 |
| hsa-miR-30c-2* | 6q13 | −1.88988 | 2.12E−06 |
| hsa-miR-130a | 11q12.1 | −1.87039 | 3.78E−05 |
| hsa-miR-557 | 1q24.2 | −1.83994 | 1.62E−03 |
| hsa-miR-551a | 1p36.32 | −1.82115 | 2.53E−03 |
| hsa-miR-637 | 19p13.3 | −1.81083 | 2.07E−02 |
| hsa-miR-518c* | 19q13.42 | −1.77801 | 4.15E−05 |
| hsa-miR-525-5p | 19q13.42 | −1.75943 | 4.76E−02 |
| hsa-miR-596 | 8p23.3 | −1.74891 | 1.75E−03 |
| hsa-miR-552* | 1p34.3 | −1.72726 | 7.31E−04 |
| hsa-miR-625* | 14q23.3 | −1.71695 | 7.00E−04 |
| hsa-miR-183* | 7q32.2 | −1.70781 | 1.41E−03 |
| hsa-miR-187* | 18q12.2 | −1.70468 | 1.12E−02 |
| hsa-miR-544 | 14 | −1.69268 | 4.74E−02 |
| hsa-miR-891a | Xq27.3 | −1.67598 | 1.29E−02 |
| hsa-miR-519e* | 19q13.42 | −1.67235 | 1.56E−02 |
| hsa-miR-933 | 2q31.1 | −1.66767 | 5.19E−05 |
| hsa-miR-939 | 8q24.3 | −1.66214 | 5.40E−03 |
| hsa-miR-214 | 1q24.3 | −1.64500 | 6.92E−03 |
| hsa-miR-671-5p | 7q36.1 | −1.64192 | 7.94E−05 |
| hsa-miR-137 | 1p21.3 | −1.63014 | 3.96E−02 |
| hsa-miR-92b* | 1q22 | −1.54966 | 4.57E−02 |
| hsa-miR-525-3p | 19q13.42 | −1.54729 | 1.45E−02 |
| hsa-miR-19a | 13q31.3 | −1.51239 | 1.90E−04 |
| hsa-miR-409-5p | 14q32.31 | −1.51024 | 5.12E−03 |

[1-10]For miRNAs that have more than one primary precursors, the chromosomal location of the first primary precursor is shown in the table. The chromosomal locations of other primary miRNAs include: 1) hsa-miR-196a-2: 12q13.13; 2) hsa-miR-29b-2: 1q32.2; 3) hsa-miR-9-2: 5q14.3, hsa-miR-9-3: 15q26.1; 4) hsa-miR-365b: 17q11.2; 5) hsa-miR-124-2: 8q12.3, hsa-miR-124-3: 20q13.33; 6) hsa-miR-219-2-5p: 9q34.11; 7) hsa-miR-135a-2: 12q23.1; 8) hsa-miR-7-2: 15q26.1, hsa-miR-7-3: 19p13.3; 9) hsa-miR-138-2: 16q13; and 10) hsa-miR-129-2-5p: 11p11.2.

Using an Illumina Genome Analyzer II (GAII) sequencing system, whole-genome small RNA sequencing was performed in glioblastoma stem cells and neural stem cells. Significantly more miRNAs were detected to be differentially expressed in glioblastoma stem cells and neural stem cells in deep sequencing analysis. For example, deep sequencing analysis revealed 105 miRNAs that were up-regulated more than 5-fold in glioblastoma stem cells. However, microarray analysis revealed only 10 miRNAs showing more than 5-fold increase in glioblastoma stem cells. Interestingly, 8 out of the 10 miRNAs that were up-regulated more than 5-fold in microarray analysis also exhibited significantly increased expression in deep sequencing analysis (Table 3). Two of the miRNAs that had more than 5-fold decrease of expression in microarray analysis also showed more than 5-fold reduction of expression in deep-sequencing analysis (Table 3). Taken together, the combined results of the microarray and deep sequencing analyses identified a set of miRNAs that are differentially expressed in glioblastoma stem cells as compared to normal neural stem cells.

TABLE 3

The miRNA signature of glioblastoma stem cells identified using both microarray and deep sequencing analyses.

| | Microarray | | Deep sequencing | |
|---|---|---|---|---|
| | Fold change | p value | Fold change | p value |
| Up-regulated | | | | |
| hsa-miR-10a | 93.65 | <1E−07 | 35,949 | 0.00E+00 |
| hsa-miR-10b | 90.38 | <1E−07 | 4,128 | 0.00E+00 |
| hsa-miR-140-5p | 12.19 | <1E−07 | 7.2 | 0.00E+00 |
| hsa-miR-204 | 9.05 | <1E−07 | 5 | 0.00E+00 |
| hsa-miR-424 | 8.38 | <1E−07 | 66 | 0.00E+00 |
| hsa-miR-34a | 7.73 | 2.00E−07 | 2.5 | 4.00E−240 |
| hsa-miR-193a-3p | 6.4 | 8.00E−06 | 93 | 9.00E−21 |
| hsa-miR-455-5p | 5.87 | 1.00E−05 | 5.3 | 5.00E−214 |
| Down-regulated | | | | |
| hsa-miR-124 | −13.37 | 8.00E−05 | −10 | 5.00E−80 |
| hsa-miR-874 | −6.76 | <1E−07 | −33 | 1.50E−98 |

Figure 2:
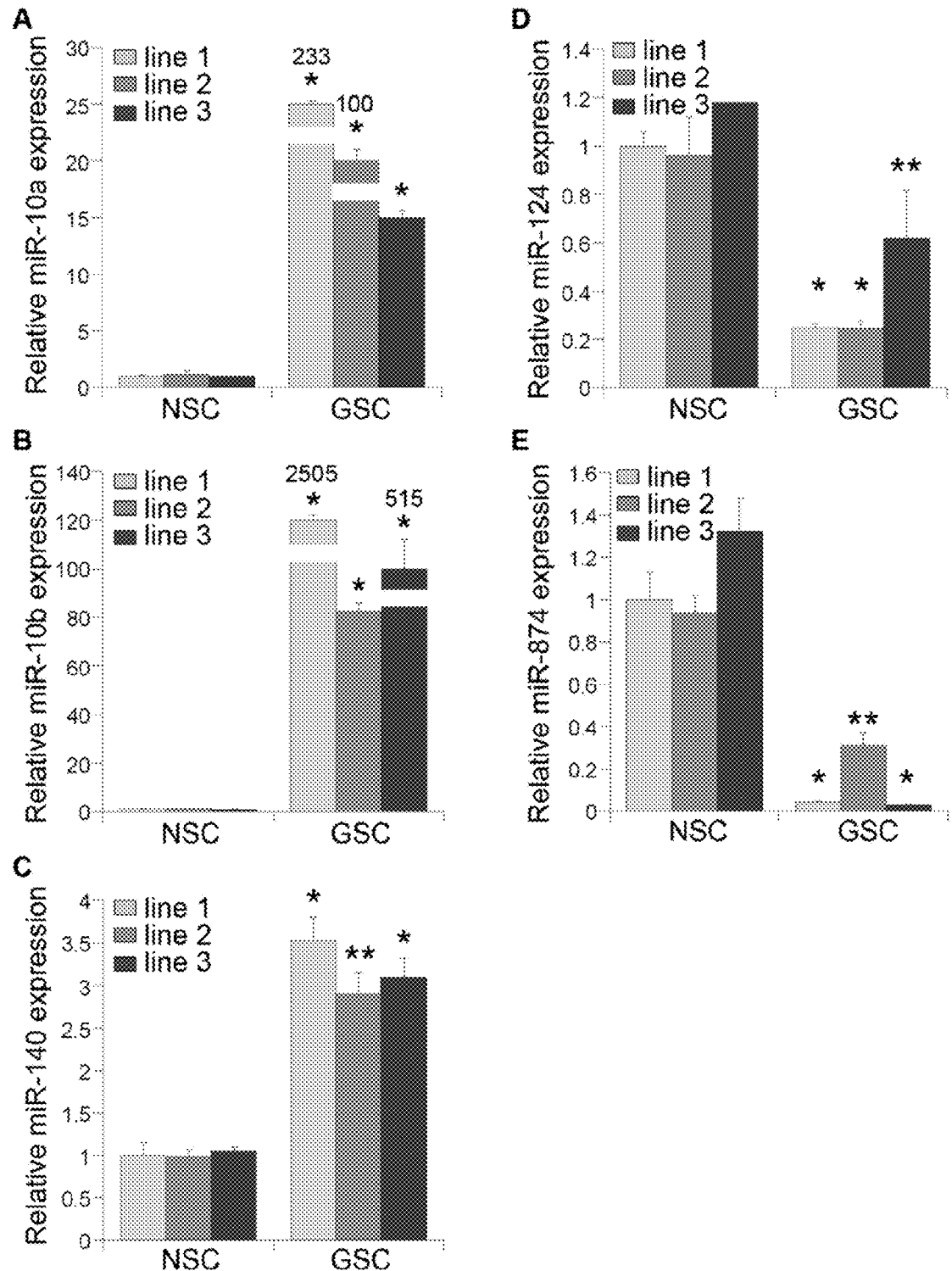
FIGS. 2A-2E illustrate the real-time RT-PCR validation of miRNA expression in glioblastoma stem cells. The expression levels of miR-10a (FIG. 2A), miR-10b (FIG. 2B), miR-140-5p (FIG. 2C), miR-124 (FIG. 2D), and miR-874 (FIG. 2E) in three glioblastoma stem cell (GSC) lines were measured by real-time RT-PCR, and compared to their expression in three neural stem cell (NSC) lines. The expression shown in each cell line is relative to the expression in NSC1, with the expression in NSC1 as 1. Error bars are standard deviation of the mean. * $p<0.001$, ** $p<0.005$ by one way ANOVA test.

Validation of the differentially expressed miRNAs using real-time RT-PCR. The distinct expression of these miRNAs in glioblastoma stem cells and neural stem cells was further validated using real-time RT-PCR analysis. RT-PCR results of the top three miRNAs that are up-regulated in glioblastoma stem cells in both microarray and deep sequencing analyses (Table 3) are shown in FIG. 2A-C. All three miRNAs showed a significant up-regulation in the three primary glioblastoma stem cell lines (GSC1-3) tested, compared to three lines of normal neural stem cells. miR-10a revealed a dramatic increase of expression in all three glioblastoma stem cell lines tested, with more than 100-fold up-regulation of expression in two of the glioblastoma stem cell lines (FIG. 2A). miR-10b exhibited even higher expression in glioblastoma stem cell lines GSC1 and GSC3, with up to 2,505-fold increase of expression in GSC1 (FIG. 2B). miR-140-5p also displayed significant increase of expression in all three glioblastoma stem cell lines tested, although with much lower fold induction (FIG. 2C).

As discussed above, two miRNAs are down-regulated more than 5-fold in glioblastoma stem cells as shown by both microarray and deep sequencing analyses. The expression of these two miRNAs was also validated using real-time RT-PCR assays. Both miR-124 and miR-874 exhibited reproducible decrease of expression in all three glioblastoma stem cell lines tested, compared to normal neural stem cells (FIG. 2D, E). Specifically, miR-874, which has not been well characterized to date, exhibited a significant reduction of expression in all three glioblastoma stem cell lines, with more than 20-fold reduction in two of the glioblastoma stem cell lines GSC1 and GSC3 (FIG. 2E).

Figure 3:
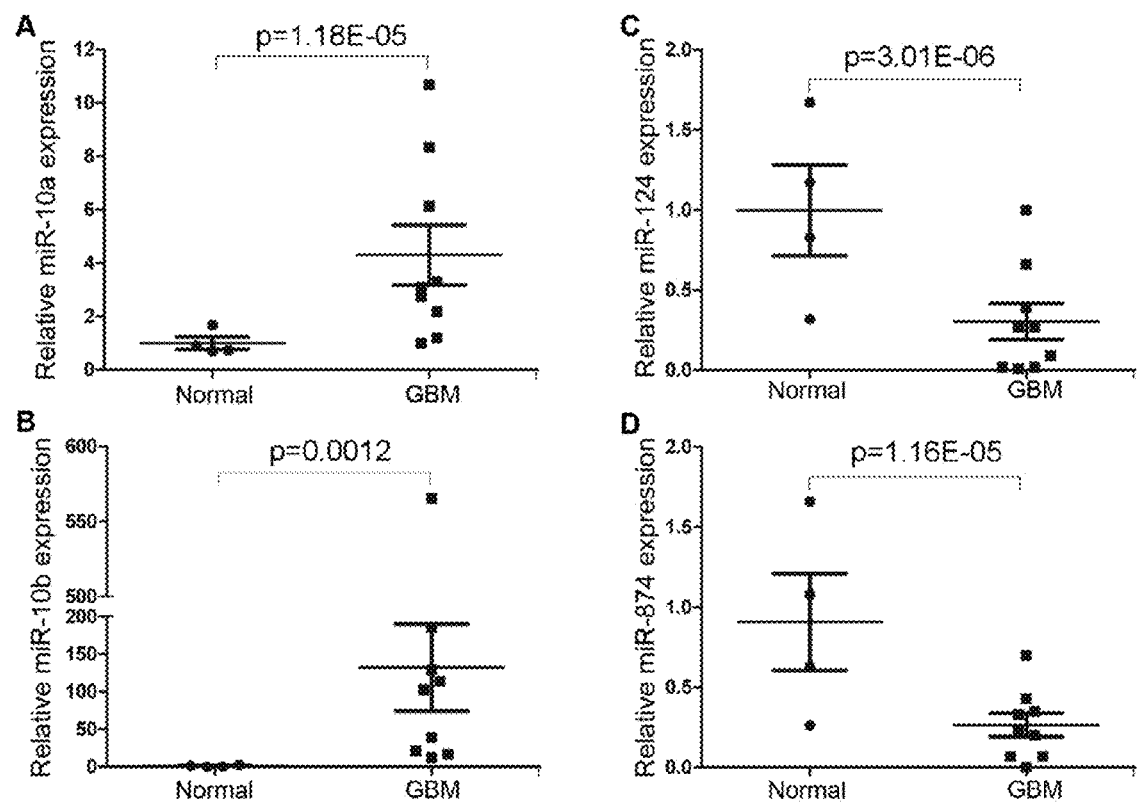
FIGS. 3A-3D illustrate the real-time RT-PCR analysis of miRNA expression in glioblastoma tissues. The expression levels of miR-10a (FIG. 3A), miR-10b (FIG. 3B), miR-124 (FIG. 3C), and miR-874 (FIG. 3D) in 9 glioblastoma tissues and 4 normal brain tissues were determine by real-time RT-PCR analysis, shown in scatted graph and bar graph. Error bars are standard error of the mean. p value was obtained by student's t-test.

In addition, normal and glioblastoma brain tissues were analyzed to determine whether the set of miRNAs identified above are differentially expressed in distinct expression patterns as shown in the cultured cell studies descried above. For this purpose, RNAs were isolated from 9 grade IV glioblastoma multiforme brain tissue samples and 4 non-tumor normal brain tissue samples. Real-time RT-PCR analyses were performed to detect the expression of two up-regulated miRNAs and two down-regulated miRNAs. Consistent with the results from tumor stem cells described above, miR-10a exhibited a substantial increase of expression in most glioblastoma tissues (FIG. 3A). miR-10b also exhibited a substantial up-regulation of expression in all of the glioblastoma tissues tested, with an average increase of 142-fold (FIG. 3B). For miRNAs that were down-regulated in glioblastoma stem cells, both miR-124 and miR-874 displayed a significant decrease of expression in most of the glioblastoma tissues tested, compared to their average expression in normal brain tissues (FIG. 3C, D).

Target Identification of the Differentially-Expressed miRNAs.

Figure 4:
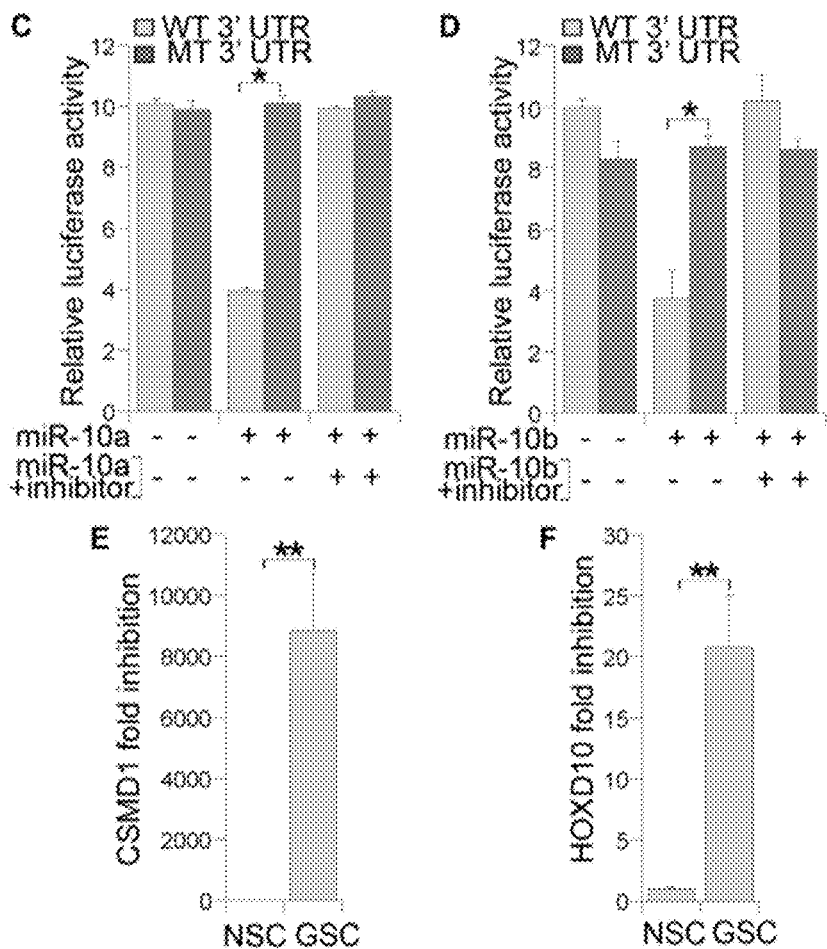
FIGS. 4A-4F illustrate the expression of miR-10b targets in glioblastoma stem cells.

By using a Targetscan algorithm [Lewis et al. 2003], CUB and SUSHI multiple domain protein 1 (CSMD1) were identified as candidate downstream targets for miR-10a and miR-10b, the most highly up-regulated miRNAs in glioblastoma stem cells in the profiling analyses. CSMD1 is a tumor suppressor gene that maps to chromosome 8p23, a region deleted in many tumor types [Kamal et al. 2010]. Sequence analysis revealed that the seed region of both miR-10a and miR-10b could form complementary base pairs with the 3' untranslated region (3' UTR) of human and mouse CSMD1 mRNAs (FIG. 4A, B). To demonstrate a direct interaction between the 3' UTR of CSMD1 and miR-10 (miR10a and miR-10b), the 3' UTR region of human CSMD1 that contains the putative miR-10 recognition sites and flanking sequences was inserted downstream of a Renilla luciferase reporter gene into a siCheck vector. RNA duplexes of mature miR-10a or miR-10b were transfected into human embryonic kidney HEK293 cells along with the reporter gene. Significant repression of the reporter gene was observed in both miR-10a and miR-10b-transfected cells (FIG. 4C, D). Mutation of the miR-10 targeting sites abolished the repression (FIG. 4C, D). Furthermore, treatment of the inhibitors of miR-10a and miR-10b reversed the inhibitory effect of miR-10a and miR-10b on the luciferase reporter activity, respectively (FIG. 4C, D). These results suggest that both miR-10a and miR-10b repress CSMD1 expression through the predicted targeting sites in CSMD1 3' UTR.

Since miR-10a and miR-10b are both up-regulated in glioblastoma stem cells relative to neural stem cells, the expression of CSMD1 was examined in both cell types. Dramatic reduction of CSMD1 mRNA expression was detected in glioblastoma stem cells by RT-PCR analysis, compared to neural stem cells (FIG. 4E), consistent with the observation that CSMD1 expression is repressed by miR-10 (FIG. 4C, D). The homeobox transcription factor HOXD10 has been identified as a tumor suppressor gene targeted by miR-10b in breast cancers [Ma et al. 2007]. Here, it was shown that the HOXD10 mRNA expression is also dramatically reduced (>20-fold) in glioblastoma stem cells examined, compared to normal neural stem cells (FIG. 4F). Together, these results suggest that miR-10 targets the expression of tumor suppressor genes, CSMD1 and HOXD10, in glioblastoma stem cells.

Figure 5:
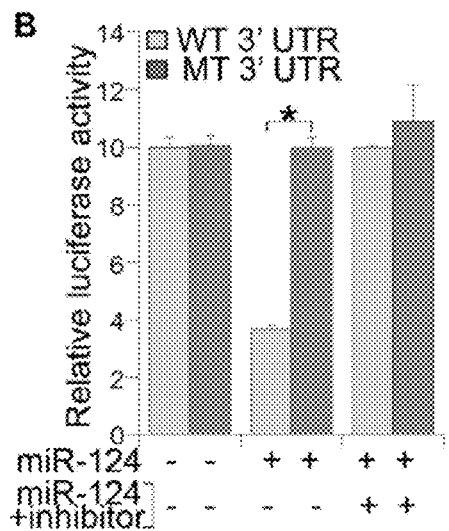
FIGS. 5A-5H show that miR-124 targets NRAS and PIM3 expression.
Figure 5:
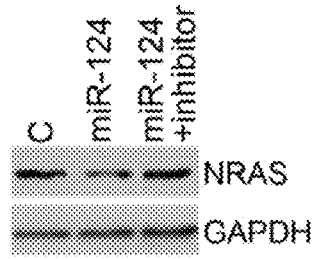
Figure 5:
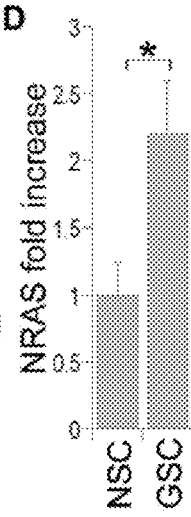
Figure 5:
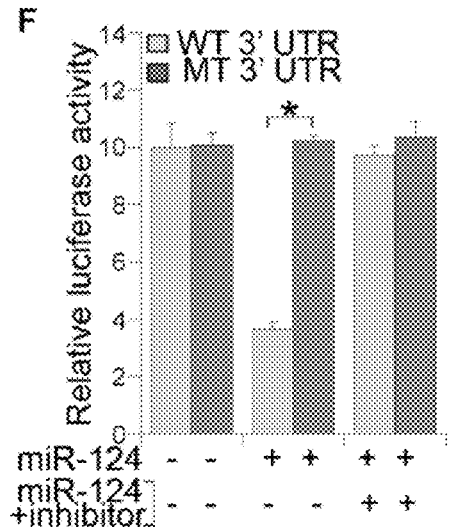
Figure 5:
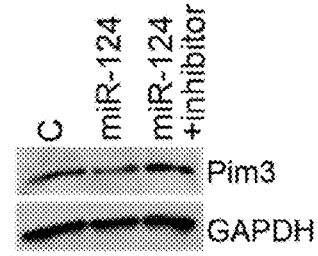
Figure 5:
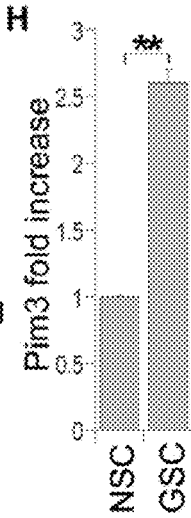

Furthermore, using the Targetscan algorithm, the oncogenes NRAS and PIM3 were selected as putative target genes of miR-124, one of the down-regulated miRNAs in glioblastoma stem cells. NRAS is a small guanine-nucleotide binding protein and one of the three RAS (KRAS, NRAS, HRAS) isoforms [Kiessling et al. 2011]. The RAS signaling pathway plays an important role in many cancers by regulating cell proliferation, differentiation, and survival [Kan et al. 2010]. Using Targetscan algorithm, miR-124 was predicted to have a targeting site at the 3' UTR of the NRAS gene. This targeting site is conserved in human, mouse, and dog NRAS (FIG. 5A). To validate the targeting of NRAS by miR-124, a luciferase reporter construct with human NRAS 3' UTR containing the predicted miR-124 targeting site was made, and the flanking sequences inserted into the 3'UTR of a Renilla luciferase reporter gene in a siCHECK vector. Transfection of miR-124 RNA duplexes led to significant repression of the reporter gene (FIG. 5B). Mutation of the putative miR-124 targeting site abolished the repression (FIG. 5B). Furthermore, treatment with a miR-124 inhibitor reversed the inhibitory effect of miR-124 on the luciferase reporter activity (FIG. 5B). These results suggest that miR-124 represses NRAS expression through the predicted targeting site in NRAS 3'UTR.

Next, it was tested whether miR-124 targets NRAS expression in glioblastoma stem cells. Mature miR-124 RNA duplexes were introduced into GSC1 cells using a cationic triethanolamine-core polyamidoamine (PAMAM) dendrimer-mediated small RNA delivery system [Zhou et al. 2006; Zhou et al. 2011]. A control RNA duplex was included as a negative control. NRAS expression levels were examined by Western blot analysis. Reduction of NRAS protein level was detected in miR-124-transfected cells. Co-transfection of a miR-124 RNA inhibitor abolished the inhibitory effect of miR-124 on NRAS expression (FIG. 5C). This result indicates that miR-124 down-regulates endogenous NRAS expression in glioblastoma stem cells.

The expression of NRAS in glioblastoma stem cells and neural stem cells was examined, where miR-124 exhibits differential expression. A significant increase of NRAS mRNA expression was detected in glioblastoma stem cells, compared to neural stem cells (FIG. 5D). The inverse expression pattern of NRAS and miR-124 is consistent with the observation that NRAS expression is repressed by miR-124 (FIG. 5B, C).

A putative targeting site of miR-124 was also identified in the 3' UTR of both human and mouse PIM3, a proto-oncogene with serine/threonine kinase activity (FIG. 5E). PIM3 has been shown to promote tumor cell growth through modulating cell cycle regulators [Wu et al. 2010; Brault et al. 2010]. To validate the targeting of PIM3 by miR-124, a luciferase reporter construct with human PIM3 3' UTR was made, which contained the predicted miR-124 targeting site and the flanking sequences inserted into the 3'UTR of a Renilla luciferase reporter gene. Transfection of miR-124 led to significant repression of the reporter gene and mutation of the putative miR-124 targeting site abolished the repression (FIG. 5F). Furthermore, treatment with a miR-124 inhibitor reversed the inhibitory effect of miR-124 on the luciferase reporter activity (FIG. 5F). These results suggest that miR-124 represses PIM3 expression through the predicted targeting site in its 3' UTR.

To test whether miR-124 targets PIM3 expression in glioblastoma stem cells, mature miR-124 RNA duplexes were introduced into GSC1 cells using the dendrimer-mediated delivery system [Zhou et al. 2006; Zhou et al. 2011]. A control RNA duplex was included as a negative control. Reduction of PIM3 protein level was detected in miR-124-transfected cells by Western blot analysis. Co-transfection of a miR-124 RNA inhibitor abolished the inhibitory effect of miR-124 on PIM3 expression (FIG. 5G). This result indicates that miR-124 down-regulates endogenous PIM3 expression in glioblastoma stem cells. Moreover, a significant increase of PIM3 mRNA expression was detected in the glioblastoma stem cells tested, compared to neural stem cells (FIG. 5H), further supporting the idea that miR-124 represses PIM3 expression.

Figure 6:
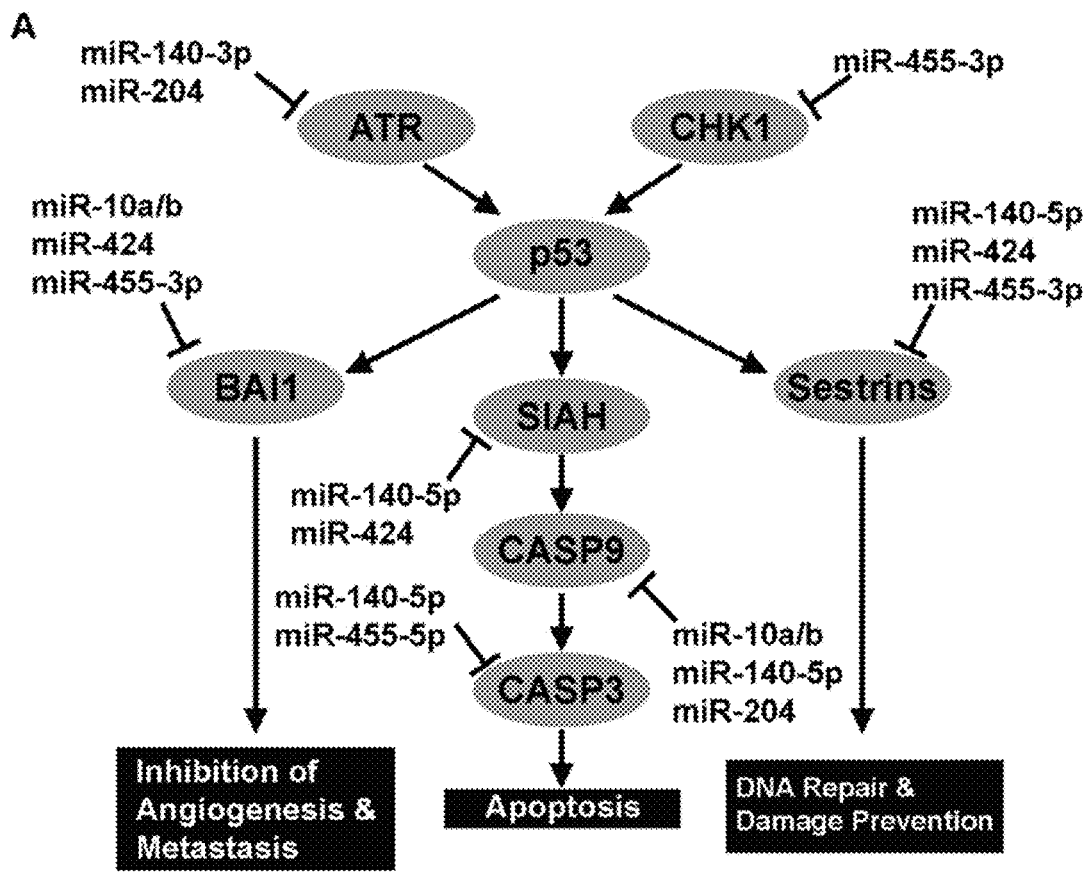
FIGS. 6A-6B show pathways targeted by deregulated miRNAs in glioblastoma stem cells. Common miRNA targets were subjected to DAVID functional annotation with KEGG pathway analysis.
Figure 6:
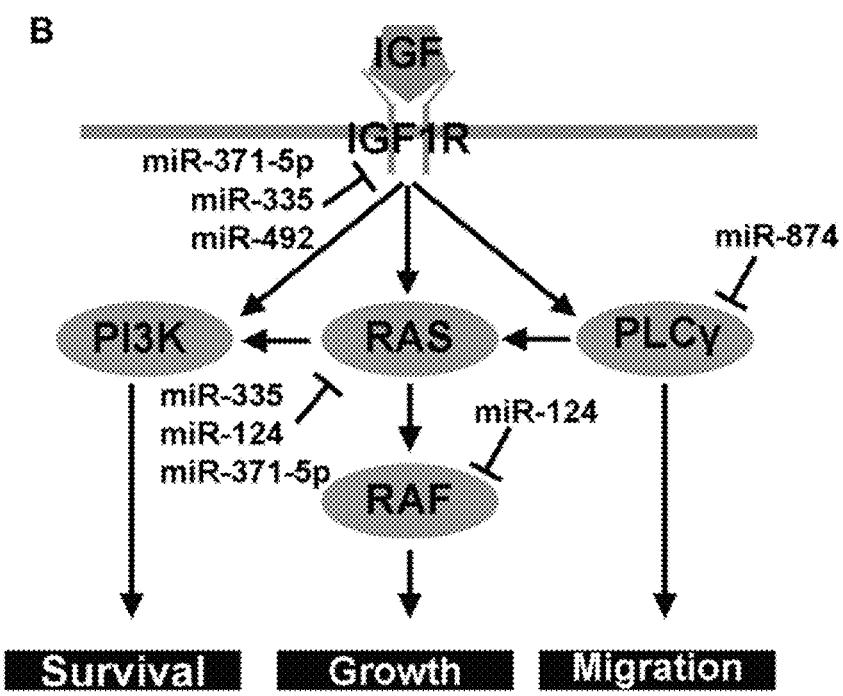

It is increasingly clear that miRNAs are important regulators of key signaling pathways implicated in tumorigenesis. Using Kyoto Encyclopedia of Genes and Genomes (KEGG) pathway analysis, the predicted targets of miRNAs that showed more than 5-fold up-regulation or down-regulation in glioblastoma stem cells in the microarray analysis were compared. Seven of the ten miRNAs that were up-regulated more than 5-fold in glioblastoma stem cells are predicted to have components of the p53 pathway as common targets (FIG. 6A). The p53 pathway has been shown to be involved in cell cycle arrest, apoptosis, inhibition of cell migration, inhibition of angiogenesis, and affect genomic stability [Junttila & Evan 2009]. In contrast, five out of eight miRNAs that exhibited more than 5-fold down-regulation in glioblastoma stem cells were predicted to target components of the IGF pathway (FIG. 6B) that has been implicated in promoting cell growth, survival and migration [Clayton et al. 2011].

Discussion

The present study investigated genome-wide miRNA expression in tumor stem cell populations of glioblastoma, the most frequent and malignant primary brain tumor. In spite of recent improvement of surgical and radiotherapeutic techniques, the prognosis for glioblastoma patients is still very poor. The search for molecular targets is fundamental to develop effective treatments for glioblastoma.

Global profiling is an effective approach to identify abnormally expressed miRNAs in tumor genomes. Three different technical platforms were used to determine the differential expression of miRNAs in glioblastoma stem cells and neural stem cells. The microarray platform was combined with the newly emerged small RNA deep sequencing technology to profile miRNA expression in glioblastoma stem cells and normal neural stem cells and validated the profiling results using quantitative RT-PCR. Although the absolute fold change obtained from each platform is different due to the different sensitivity of the techniques, the trend of the change for the miRNAs studied is consistent. The miRNA expression profile could clearly distinguish glioblastoma stem cells from normal neural stem cells, allowing us to identify a miRNA signature of glioblastoma stem cells that were significantly up-regulated or down-regulated in glioblastoma stem cells, relative to neural stem cells.

In line with the findings that a set of miRNAs are differentially expressed in glioblastoma stem cells and normal neural stem cells, certain miRNAs also exhibit distinct expression profiles in glioblastoma tissues and normal brain tissues. For example, it was demonstrated that the expression of miR-874 is dramatically reduced in glioblastoma tissues, compared to normal brain tissues. miR-124, another miRNA that was down-regulated in glioblastoma stem cells, also exhibited reduced expression in glioblastoma tissues in this study, consistent with the results of previous glioblastoma tumor tissue profiling [Huse et al. 2009; Silber et al. 2008; Clafre et al. 2005; Godlewski et al. 2008; Xia et al. 2012; Skalsky & Cullen 2011; Fowler et al. 2011].

In this study, miR-10b was shown to be highly expressed in both glioblastoma stem cells and in glioblastoma tumor tissues. Up-regulation of miR-10b was also observed in other glioblastoma samples [H use et al. 2009; Clafre et al. 2005; Godlewski et al. 2008], suggesting an important role for miR-10b in glioblastoma tumorigenesis. Moreover, a recent study revealed that miR-10b expression is inversely correlated with glioblastoma patient survival [Gabriely et al. 2011]. Interestingly, miR-10b was also found to be up-regulated in breast cancer, leukemia, and pancreatic cancer and promote tumor invasion and metastasis in breast cancer [Ma et al. 2007; Cahn et al. 2004; Bloomston et al. 2007]. Together, these results suggest that some miRNAs, such as miR-10b, may function as a global oncogene to stimulate tumorigenesis in multiple tissues. Likewise, miR-124 is also frequently down-regulated in other cancers, such as medulloblastoma, hepatocellular carcinoma, and oral squamous carcinoma [Li et al. 2009; Furuta et al. 2010; Hunt et al. 2011], suggesting that it may function as a general tumor suppressor. Therefore the knowledge of miRNAs that we have obtained for glioblastoma stem cells may be applicable to other types of cancer stem cells.

Pathway analysis revealed that most of the significantly up-regulated miRNAs, with more than 5-fold increase in glioblastoma stem cells as shown in the microarray analysis described herein, have putative targets in a common pathway, the p53 pathway. The dysregulation of the p53 pathway has been shown to be an underlying mechanism for tumorigenesis [Junttila & Evan 2009], thus the up-regulated miRNAs may function as oncomiRs by targeting the p53 pathway if their role in regulating the p53 pathway is confirmed. On the other hand, most of the down-regulated miRNAs, with more than 5-fold decrease in glioblastoma stem cells, share their predicted targets in the IGF signaling. Repression of the IGF signaling has been shown to inhibit tumorigenesis [Clayton et al. 2011]. Thus, these down-regulated miRNAs may assume a role of tumor suppressors by targeting components of the IGF pathway if their role in regulating the IGF signaling is confirmed. The identification of miRNAs as oncogenes or tumor suppressors holds the promise of identifying novel diagnostic markers or molecular targets for antitumor therapies. The prediction that the differentially expressed miRNAs have the ability to target multiple components in one or more pathways makes them potential molecular targets for cancer therapy.

Glioblastoma stem cells represent a subpopulation of cancer cells with extraordinary capacities to promote tumor growth, invasion and therapeutic resistance, making them an ideal target cell population for anti-glioblastoma therapies. However, a major challenge is to define functional and molecular features that can distinguish cancer stem cells from normal stem cells in order to develop therapeutic strategies that specifically target the tumor population, but leave normal stem cells intact. Therefore comparing miRNA expression between glioblastoma stem cells and normal neural stem cells is highly relevant in that it may lead to the identification of glioblastoma stem cell-specific miRNAs, thus resulting in the development of novel glioblastoma therapies by targeting only tumor stem cells. A comparison of the miRNA expression between glioblastoma stem cells from adult glioblastoma patients and normal neural stem cells from human fetal brains was performed. Fetal brains were used instead of human adult brains due to the inaccessibility of normal human adult brain tissues containing neural stem cells. Although differences do exist between embryonic neural stem cells and adult neural stem cells, it has been proposed that embryonic neural stem cells resemble adult neural stem cells in many ways [Ming & Song 2011]. Therefore this comparison will provide useful information regarding glioblastoma stem cell-specific miRNA expression and provide a basis for strategic targeting glioblastoma stem cells through modulation of tumor stem cell-specific miRNA expression.

miRNAs have been shown to be involved in tumor initiation and progression, functioning as oncogenes or tumor suppressor [Asadi-Moghaddam et al. 2010; Cheng et al. 2010]. Therefore, modulation of miRNA expression provides great hope for potential cancer therapy [Verissimo et al. 2011]. Furthermore, since each miRNA may have more than one targets, miRNA-based gene therapy offers the therapeutic appeal of targeting multiple gene networks that are controlled by a single miRNA [Asadi-Moghaddam et al. 2010]. Strategies for miRNA-based cancer therapy include overexpression of tumor suppressor miRNAs and targeting oncogenic miRNAs using their antagonists. Based on the miRNA signature that was identified in glioblastoma stem cells, targeted glioblastoma therapies may be developed by inhibiting the up-regulated miR-10a or miR-10b function using miR-10 antagonists or overexpressing the down-regulated miR-124 or miR-874. Of note, 16 miRNAs that were up-regulated in glioblastoma stem cells (>1.5-fold, as shown in Table 2), including miR-10a and miR-10b, are also up-regulated in malignant astrocytomas (glioblastomas and anaplastic astrocytomas) in a genome-wide miRNA expression profiling between malignant astrocytomas and normal brain samples [Rao et al. 2010]. Eleven miRNAs that were down-regulated in glioblastoma stem cells (>1.5-fold, as shown in Table 2), including miR-124, are also down-regulated in malignant astrocytomas.

Moreover, the prognosis of glioblastoma patients remains poor. Biomarkers for this disease are needed for early detection of tumor progression [Roth et al. 2011]. The miRNA signature that was identified herein may be used as biomarkers to differentiate glioblastoma stem cells from normal neural stem cells. Recently, an miRNA signature was identified in the peripheral blood of glioblastoma patients [Roth et al. 2011]. Interestingly, several of the miRNAs that showed elevated expression in the blood samples of glioblastoma patients (vs healthy control) also exhibited increased expression in glioblastoma stem cells (vs normal neural stem cells) in the study described herein (Table 2), including miR-424, miR-148a, miR-362-3p, miR-30d, miR-128. These miRNAs may therefore represent easily accessible biomarkers that can be used for diagnostic purposes in glioblastoma patients.

Example 2 miR-874 Acts as a Tumor Suppressor to Target and Suppress Glioblastoma Stem Cells In the studies described above, an miRNA profiling analysis using both microarray and deep sequencing analyses revealed that one of the miRNAs—miR-874—was significantly down-regulated in glioblastoma stem cells (GSCs) relative to normal stem cells (NSCs). These studies suggest that this miRNA may function as a tumor suppressor. As such, the role of miR-874 in GSC growth was characterized in a study using two GSC cell lines derived from WHO grade IV glioblastoma patients, PBT017 and PBT707. A lentiviral expression system was used to deliver miR-874 to the two GCS cells lines.

Figure 7:
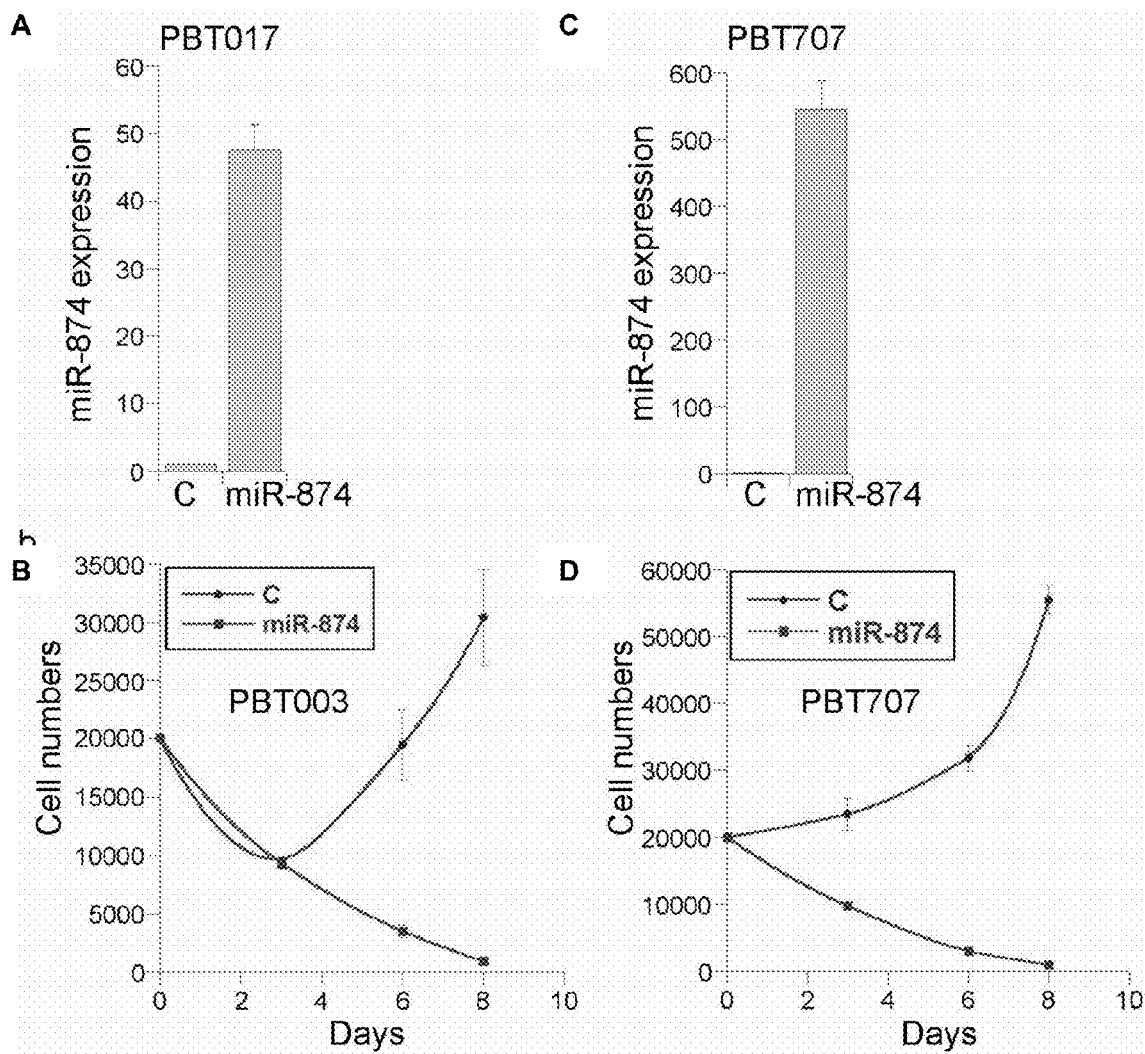
FIGS. 7A-7D illustrate viral transduction of miR-874 in glioblastoma lines PBT017 and PBT707 (FIGS. 7A and 7C, respectively), and resulting reduced growth of the PBT017 and PBT707 glioblastoma cells due to expression of miR-874 (FIGS. 7B and 7D, respectively).

Transduction of the GSC lines with miR-874-expressing lentivirus led to robust expression of miR-874 in both types of cells, as shown in FIG. 7A (PBT017 cells) and FIG. 7C (PBT707 cells). The PBT017 and PBT707 cells overexpressing miR-874 were cultured for approximately 8-10 days to observe miR-874's effect on cell growth. A growth curve analysis revealed that overexpression of miR-874 led to dramatically reduced cell numbers in both PBT017 and PBT707 glioblastoma stem cell lines, as shown in FIGS. 7B and 7D. These results suggest that miR-874 may act as a potential tumor suppressor miRNA and may be used in accordance with the methods for treating cancers (e.g., glioblastoma) described herein.

REFERENCES

The references, patents and published patent applications listed below, and all references cited in the specification above are hereby incorporated by reference in their entirety, as if fully set forth herein.

Ambros V (2004) The functions of animal microRNAs. Nature 431: 350-355.

Asadi-Moghaddam K, Chiocca E A, Lawler S E (2010) Potential role of miRNAs and their inhibitors in glioma treatment. Expert review of anticancer therapy 10: 1753-1762.

Bao S, Wu Q, McLendon R E, Hao Y, Shi Q, et al. (2006) Glioma stem cells promote radioresistance by preferential activation of the DNA damage response. Nature 444: 756-760.

Bartel D P (2004) MicroRNAs: genomics, biogenesis, mechanism, and function. Cell 116: 281-297.

Bloomston M, Frankel W L, Petrocca F, Volinia S, Alder H, et al. (2007) MicroRNA expression patterns to differentiate pancreatic adenocarcinoma from normal pancreas and chronic pancreatitis. Jama 297: 1901-1908.

Brault L, Gasser C, Bracher F, Huber K, Knapp S, et al. (2010) PIM serine/threonine kinases in the pathogenesis and therapy of hematologic malignancies and solid cancers. Haematologica 95: 1004-1015.

Brown C E, Starr R, Martinez C, Aguilar B, D'Apuzzo M, et al. (2009) Recognition and killing of brain tumor stem-like initiating cells by CD8+ cytolytic T cells. Cancer research 69: 8886-8893.

Cahn G A, Liu C G, Sevignani C, Ferracin M, Felli N, et al. (2004) MicroRNA profiling reveals distinct signatures in B cell chronic lymphocytic leukemias. Proceedings of the National Academy of Sciences of the United States of America 101: 11755-11760.

Cheng L, Bao S, Rich J N (2010) Potential therapeutic implications of cancer stem cells in glioblastoma. Biochemical pharmacology 80: 654-665.

Ciafre S A, Galardi S, Mangiola A, Ferracin M, Liu C G, et al. (2005) Extensive modulation of a set of microRNAs in primary glioblastoma. Biochemical and biophysical research communications 334: 1351-1358.

Clayton P E, Banerjee I, Murray P G, Renehan A G (2011) Growth hormone, the insulin-like growth factor axis, insulin and cancer risk. Nat Rev Endocrinol 7: 11-24.

Conti A, Aguennouz M, La Torre D, Tomasello C, Cardali S, et al. (2009) miR-21 and 221 upregulation and miR-181b downregulation in human grade II-IV astrocytic tumors. Journal of neuro-oncology 93: 325-332.

Ebert M S, Neilson J R, Sharp P A, (2007) MicroRNA sponges: competitive inhibitors of small RNAs in mammalian cells. Nat. Methods. 4(9):721-6.

Esquela-Kerscher A, Slack F J (2006) Oncomirs—microRNAs with a role in cancer. Nat Rev Cancer 6: 259-269.

Fowler A, Thomson D, Giles K, Maleki S, Mreich E, et al. (2011) miR-124a is frequently down-regulated in glioblastoma and is involved in migration and invasion. Eur J Cancer 47: 953-963.

Furuta M, Kozaki K I, Tanaka S, Arii S, Imoto I, et al. (2010) miR-124 and miR-203 are epigenetically silenced tumor-suppressive microRNAs in hepatocellular carcinoma. Carcinogenesis 31: 766-776.

Gabriely G, Yi M, Narayan R S, Niers J M, Wurdinger T, et al. (2011) Human glioma growth is controlled by microRNA-10b. Cancer research 71: 3563-3572.

Gal H, Pandi G, Kanner A A, Ram Z, Lithwick-Yanai G, et al. (2008) MIR-451 and Imatinib mesylate inhibit tumor growth of Glioblastoma stem cells. Biochemical and biophysical research communications 376: 86-90.

Godlewski J, Newton H B, Chiocca E A, Lawler S E (2010) MicroRNAs and glioblastoma; the stem cell connection. Cell death and differentiation 17: 221-228.

Godlewski J, Nowicki M O, Bronisz A, Williams S, Otsuki A, et al. (2008) Targeting of the Bmi-1 oncogene/stem cell renewal factor by microRNA-128 inhibits glioma proliferation and self-renewal. Cancer research 68: 9125-9130.

Hunt S, Jones A V, Hinsley E E, Whawell S A, Lambert D W (2011) MicroRNA-124 suppresses oral squamous cell carcinoma motility by targeting ITGB1. FEBS letters 585: 187-192.

Huse J T, Brennan C, Hambardzumyan D, Wee B, Pena J, et al. (2009) The PTEN-regulating microRNA miR-26a is amplified in high-grade glioma and facilitates gliomagenesis in vivo. Genes & development 23: 1327-1337.

Junttila M R, Evan G I (2009) p53—a Jack of all trades but master of none. Nat Rev Cancer 9: 821-829.

Kamal M, Shaaban A M, Zhang L, Walker C, Gray S, et al. (2010) Loss of CSMD1 expression is associated with high tumour grade and poor survival in invasive ductal breast carcinoma. Breast cancer research and treatment 121: 555-563.

Kan Z, Jaiswal B S, Stinson J, Janakiraman V, Bhatt D, et al. (2010) Diverse somatic mutation patterns and pathway alterations in human cancers. Nature 466: 869-873.

Kiessling M K, Oberholzer P A, Mondal C, Karpova M B, Zipser M C, et al. (2011) High-throughput mutation profiling of CTCL samples reveals KRAS and NRAS mutations sensitizing tumors toward inhibition of the RAS/RAF/MEK signaling cascade. Blood 117: 2433-2440.

Kim H, Huang W, Jiang X, Pennicooke B, Park P J, et al. (2010) Integrative genome analysis reveals an oncomir/oncogene cluster regulating glioblastoma survivorship. Proceedings of the National Academy of Sciences of the United States of America 107: 2183-2188.

Lewis B P, Shih I H, Jones-Rhoades M W, Bartel D P, Burge C B (2003) Prediction of mammalian microRNA targets. Cell 115: 787-798.

Li K K, Pang J C, Ching A K, Wong C K, Kong X, et al. (2009) miR-124 is frequently down-regulated in medulloblastoma and is a negative regulator of SLC16A1. Human pathology 40: 1234-1243.

Louis D N, Ohgaki H, Wiestler O D, Cavenee W K, Burger P C, et al. (2007) The 2007 WHO classification of tumours of the central nervous system. Acta neuropathologica 114: 97-109.

Ma L, Teruya-Feldstein J, Weinberg R A (2007) Tumour invasion and metastasis initiated by microRNA-10b in breast cancer. Nature 449: 682-688.

Ming G L, Song H (2011) Adult neurogenesis in the mammalian brain: significant answers and significant questions. Neuron 70: 687-702.

Rao S A, Santosh V, Somasundaram K (2010) Genome-wide expression profiling identifies deregulated miRNAs in malignant astrocytoma. Mod Pathol 23: 1404-1417.

Roth P, Wischhusen J, Happold C, Chandran P A, Hofer S, et al. (2011) A specific miRNA signature in the peripheral blood of glioblastoma patients. Journal of neurochemistry 118: 449-457.

Shi Y, Zhao X, Hsieh J, Wichterle H, Impey S, et al. (2010) MicroRNA regulation of neural stem cells and neurogenesis. J Neuroscience 30: 14931-14936.

Silber J, Lim D A, Petritsch C, Persson A I, Maunakea A K, et al. (2008) miR-124 and miR-137 inhibit proliferation of glioblastoma multiforme cells and induce differentiation of brain tumor stem cells. BMC medicine 6: 14.

Singh S K, Hawkins C, Clarke I D, Squire J A, Bayani J, et al. (2004) Identification of human brain tumour initiating cells. Nature 432: 396-401.

Skalsky R L, Cullen B R (2011) Reduced expression of brain-enriched microRNAs in glioblastomas permits targeted regulation of a cell death gene. PloS one 6: e24248.

Sun G, Ye P, Murai K, Lang, M-F, Li S, et al. (2011) miR-137 forms a regulatory loop with nuclear receptor TLX and LSD1 in neural stem cells. Nature Communications 2: 529. DOI:10.1038/ncomms1532.

Sun G, Yu R, Evans R M, Shi Y. (2007) Orphan nuclear receptor TLX recruits histone deacetylases to repress transcription and regulate neural stem cell proliferation. Proceedings of the National Academy of Sciences of the United States of America 104: 15282-15287.

Verissimo C S, Molenaar J J, Fitzsimons C P, Vreugdenhil E (2011) Neuroblastoma therapy: what is in the pipeline? Endocrine-related cancer 18: R213-231.

Wu Y, Wang Y Y, Nakamoto Y, Li Y Y, Baba T, et al. (2010) Accelerated hepatocellular carcinoma development in mice expressing the Pim-3 transgene selectively in the liver. Oncogene 29: 2228-2237.

Xia H, Cheung W K, Ng S S, Jiang X, Jiang S, et al. (2012) Loss of brain-enriched miR-124 enhances the stem-like traits and invasiveness of glioma cells. The Journal of biological chemistry.

Zhao C, Sun G, Li S, Lang M-F, Yang S, Li W, Shi Y. (2010) MicroRNA let-7b regulates neural stem cell proliferation and differentiation by targeting nuclear receptor TLX signaling. Proceedings of the National Academy of Sciences of the United States of America 107: 1876-1881.

Zhao C, Sun G, Li S, Shi Y. (2009) A feedback regulatory loop involving microRNA-9 and nuclear receptor TLX in neural stem cell fate determination. Nature Structural & Molecular Biology 16: 365-371.

Zhou J, Neff C P, Liu X, Zhang J, Li H, et al. (2011) Systemic administration of combinatorial dsiRNAs via nanoparticles efficiently suppresses HIV-1 infection in humanized mice. Mol Ther 19: 2228-2238.

Zhou J, Wu J, Hafdi N, Behr J-P, Erbacher P, et al. (2006) PAMAM dendrimers for efficient siRNA delivery and potent gene silencing. Chem Commun 22: 2362-2364.

What is claimed is:

1. A method of treating a glioblastoma comprising:
administering a therapeutically effective amount of a pharmaceutical composition to a subject having the glioblastoma,
wherein the pharmaceutical composition comprises at least one miRNA molecule that is down regulated in a stem cell of the glioblastoma compared to a normal neural stem cell, a vector capable of expressing said at least one miRNA molecule in a glioblastoma stem cell, or a combination thereof,
and wherein the at least one miRNA molecule that is down regulated in the glioblastoma stem cell compared to a normal neural stem cell is a miR-874 molecule.

2. The method of claim 1 further comprising administering to the subject at least one miRNA inhibitor that inhibits the activity of a miRNA molecule that is upregulated in the glioblastoma stem cell as compared to the normal neural stem cell, wherein the miRNA inhibitor comprises a nucleic acid that is sufficiently complementary to the miRNA molecule to hybridize to the miRNA molecule under physiological conditions.

3. The method of claim 2, wherein the upregulated miRNA is selected from miR-10a, miR-10b, miR-140-3p, miR-140-5p, miR-204, miR-424, miR-34a, miR-193a-3p, miR-455-5p, miR-455-3p, miR-9, miR-10a, miR-148a, miR-488, miR-196a1, miR-182, miR-96, miR-193b, miR-27a, miR-196b, miR-10b, miR-29b2, miR-23a, miR-107, miR-542-3p, miR-93, miR-365a4, miR-450a, miR-100, miR-105, miR-363, miR-105, miR-106b, miR-15b, miR-21, miR-376c, miR-93, miR-99b, miR-155, miR-33a, miR-876-3p, miR-362-3p, miR-25, let-7i, miR-423-3p, miR-34b, miR-16-2, miR-29a, miR-30d, miR-320, miR-181c, miR-128a, miR-21, let-7d, and miR-450b-5p.

4. The method of claim 1 wherein the at least one miRNA molecule that is down regulated in a glioblastoma stem cell compared to a normal neural stem cell further comprises one or more miRNA molecules selected from the group consisting of miR-371-5p, miR-1245, miR-335, miR-492, miR-30b, miR-193a-5p, miR-602, miR-346, miR-663, miR-25, miR-219-5p6, miR-184, miR-135a7, miR-584, miR-665, miR-638, miR-503, miR-628-3p, miR-381, miR-78, miR-92b, miR-149, miR-135b, miR-302d, miR-498, miR-766, miR-1389, miR-623, miR-519c-5p, miR-182, miR-494, miR-129-5p10, miR-513-5p, miR-200b, miR-634, miR-654-5p, miR-518b, miR-658, miR-373, miR-30c-2, miR-130a, miR-557, miR-551a, miR-637, miR-518c, miR-525-5p, miR-596, miR-552, miR-625, miR-183, miR-187, miR-544, miR-891a, miR-519e, miR-933, miR-939, miR-214, miR-671-5p, miR-137, miR-92b, miR-525-3p, miR-19a, and miR-409-5p.

* * * * *

SEQUENCE LISTING

<160> NUMBER OF SEQ ID NOS: 35

<210> SEQ ID NO 1
<211> LENGTH: 23
<212> TYPE: RNA
<213> ORGANISM: Artificial Sequence
<220> FEATURE:
<223> OTHER INFORMATION: Synthetic oligonucleotide: hsa-miR-10a

<400> SEQUENCE: 1
uacccuguag auccgaauuu gug    23

```
<210> SEQ ID NO 2
<211> LENGTH: 22
<212> TYPE: RNA
<213> ORGANISM: Homo sapiens
<220> FEATURE:
<221> NAME/KEY: misc_feature
<223> OTHER INFORMATION: human CSMD1 693

<400> SEQUENCE: 2
aauaaauuau uuacacaggg uu                                           22

<210> SEQ ID NO 3
<211> LENGTH: 18
<212> TYPE: RNA
<213> ORGANISM: Mus spicilegus
<220> FEATURE:
<221> NAME/KEY: misc_feature
<223> OTHER INFORMATION: mouse CSMD1 701

<400> SEQUENCE: 3
aacaauuucc acaggguu                                                18

<210> SEQ ID NO 4
<211> LENGTH: 23
<212> TYPE: RNA
<213> ORGANISM: Homo sapiens
<220> FEATURE:
<221> NAME/KEY: misc_feature
<223> OTHER INFORMATION: human CSMD1 2143

<400> SEQUENCE: 4
cgugugcaag ggagaacagg guu                                          23

<210> SEQ ID NO 5
<211> LENGTH: 23
<212> TYPE: RNA
<213> ORGANISM: Mus spicilegus
<220> FEATURE:
<221> NAME/KEY: misc_feature
<223> OTHER INFORMATION: mouse CSMD1 2063

<400> SEQUENCE: 5
agugcguaag ggagaacagg guu                                          23

<210> SEQ ID NO 6
<211> LENGTH: 23
<212> TYPE: RNA
<213> ORGANISM: Artificial Sequence
<220> FEATURE:
<223> OTHER INFORMATION: Synthetic oligonucleotide: hsa-miR-10b

<400> SEQUENCE: 6
uacccuguag aaccgaauuu gug                                          23

<210> SEQ ID NO 7
<211> LENGTH: 20
<212> TYPE: RNA
<213> ORGANISM: Artificial Sequence
<220> FEATURE:
<223> OTHER INFORMATION: Synthetic oligonucleotide: hsa-miR-124

<400> SEQUENCE: 7
uaaggcacgc ggugaaugcc                                              20

<210> SEQ ID NO 8
<211> LENGTH: 23
<212> TYPE: RNA
```

```
<213> ORGANISM: Homo sapiens
<220> FEATURE:
<221> NAME/KEY: misc_feature
<223> OTHER INFORMATION: human NRAS 625

<400> SEQUENCE: 8
aacuuucaca gugaagugcc uuu                                             23

<210> SEQ ID NO 9
<211> LENGTH: 23
<212> TYPE: RNA
<213> ORGANISM: Mus spicilegus
<220> FEATURE:
<221> NAME/KEY: misc_feature
<223> OTHER INFORMATION: mouse NRAS 585

<400> SEQUENCE: 9
aacauucaca acaaagugcc uuu                                             23

<210> SEQ ID NO 10
<211> LENGTH: 23
<212> TYPE: RNA
<213> ORGANISM: Canis lupus
<220> FEATURE:
<221> NAME/KEY: misc_feature
<223> OTHER INFORMATION: dog NRAS 637

<400> SEQUENCE: 10
aacucuugca gcaaagugcc uuu                                             23

<210> SEQ ID NO 11
<211> LENGTH: 22
<212> TYPE: RNA
<213> ORGANISM: Homo sapiens
<220> FEATURE:
<221> NAME/KEY: misc_feature
<223> OTHER INFORMATION: human PIM3 127

<400> SEQUENCE: 11
gaccuucgcu uugagugccu uu                                              22

<210> SEQ ID NO 12
<211> LENGTH: 22
<212> TYPE: RNA
<213> ORGANISM: Mus spicilegus
<220> FEATURE:
<221> NAME/KEY: misc_feature
<223> OTHER INFORMATION: mouse PIM3 104

<400> SEQUENCE: 12
gaccuuugcu uugagugccu uu                                              22

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide: CSMD1 forward

<400> SEQUENCE: 13
gatcctcgag ctgttctgtc gcagaatg                                        28

<210> SEQ ID NO 14
<211> LENGTH: 31
<212> TYPE: DNA
<213> ORGANISM: Artificial Sequence
<220> FEATURE:
```

```
<223> OTHER INFORMATION: Synthetic oligonucleotide: CSMD1 reverse

<400> SEQUENCE: 14
gatcgcggcc gcgtcagcat tttgcaccta g                              31

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide: PIM3 forward

<400> SEQUENCE: 15
gatcctcgag gcttgtgagg agctgcac                                  28

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide: PIM3 reverse

<400> SEQUENCE: 16
gatcgcggcc gcggaaactt gtcaggtcac c                              31

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide: NRAS forward

<400> SEQUENCE: 17
gatcctcgag ctggaggaga agtattcctg                                30

<210> SEQ ID NO 18
<211> LENGTH: 33
<212> TYPE: DNA
<213> ORGANISM: Artificial Sequence
<220> FEATURE:
<223> OTHER INFORMATION: Synthetic oligonucleotide: NRAS reverse

<400> SEQUENCE: 18
gatcgcggcc gctgcaaatg tagagctttc tgg                            33

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide: miR-10a RNA duplex
      sense sequence

<400> SEQUENCE: 19
taccctgtag atccgaattt gtg                                       23

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide: miR-10b RNA duplex
      sense sequence

<400> SEQUENCE: 20
taccctgtag aaccgaattt gtg                                       23
```

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide: miR-124 RNA duplex
      sense sequence

<400> SEQUENCE: 21
taaggcacgc ggtgaatgcc                                                 20

<210> SEQ ID NO 22
<211> LENGTH: 24
<212> TYPE: RNA
<213> ORGANISM: Artificial Sequence
<220> FEATURE:
<223> OTHER INFORMATION: Synthetic oligonucleotide: control RNA duplex
      sense sequence

<400> SEQUENCE: 22
ucacaaccuc cuagaaagag uaga                                            24

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide: PIM3 forward

<400> SEQUENCE: 23
agctcaagct catcgacttc                                                 20

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide: PIM3 reverse

<400> SEQUENCE: 24
tagcggtggt agcggatc                                                   18

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide: NRAS forward

<400> SEQUENCE: 25
ccatgagaga ccaatacatg ag                                              22

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide: NRAS reverse

<400> SEQUENCE: 26
gcttaatctg ctccctgtag                                                 20

<210> SEQ ID NO 27
<211> LENGTH: 19
<212> TYPE: DNA

```
<213> ORGANISM: Artificial Sequence
<220> FEATURE:
<223> OTHER INFORMATION: Synthetic oligonucleotide: HOXD10 forward

<400> SEQUENCE: 27
ttcccgaaga gaggagctg                                              19

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide: HOXD10 reverse

<400> SEQUENCE: 28
ctgccactct ttgcagtgag                                             20

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide: CSMD1 forward

<400> SEQUENCE: 29
gcagaaatgc ttactgagga tg                                          22

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide: CSMD1 reverse

<400> SEQUENCE: 30
agaaccctca aactgcaact g                                           21

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide: GAPDH forward

<400> SEQUENCE: 31
atcaccatct tccaggagc                                              19

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide: GAPDH reverse

<400> SEQUENCE: 32
ccttctccat ggtggtgaag                                             20

<210> SEQ ID NO 33
<211> LENGTH: 23
<212> TYPE: RNA
<213> ORGANISM: Artificial Sequence
<220> FEATURE:
<223> OTHER INFORMATION: Synthetic oligonucleotide: hsa-miR-10a

<400> SEQUENCE: 33
guguuuaagc cuagaugucc cau                                         23
```

```
<210> SEQ ID NO 34
<211> LENGTH: 23
<212> TYPE: RNA
<213> ORGANISM: Artificial Sequence
<220> FEATURE:
<223> OTHER INFORMATION: Synthetic oligonucleotide: hsa-miR-10b

<400> SEQUENCE: 34
guguuuaagc caagaugucc cau                                              23

<210> SEQ ID NO 35
<211> LENGTH: 20
<212> TYPE: RNA
<213> ORGANISM: Artificial Sequence
<220> FEATURE:
<223> OTHER INFORMATION: Synthetic oligonucleotide: hsa-miR-124

<400> SEQUENCE: 35
ccguaagugg cgcacggaau                                                  20
```